US010806384B2

United States Patent
Frey et al.

(10) Patent No.: US 10,806,384 B2
(45) Date of Patent: Oct. 20, 2020

(54) KIT FOR DETERMINING AN ANALYTE CONCENTRATION

(71) Applicant: Roche Diabetes Care, Inc, Indianapolis, IN (US)

(72) Inventors: Stephan-Michael Frey, Pfungstadt (DE); Oliver Kube, Worms (DE); Wolfgang Heck, Frankenthal (DE); Helmut Walter, Heppenheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 299 days.

(21) Appl. No.: 15/754,756

(22) PCT Filed: Sep. 1, 2016

(86) PCT No.: PCT/EP2016/070645
§ 371 (c)(1),
(2) Date: Feb. 23, 2018

(87) PCT Pub. No.: WO2017/037191
PCT Pub. Date: Mar. 9, 2017

(65) Prior Publication Data
US 2019/0374138 A1 Dec. 12, 2019

(30) Foreign Application Priority Data
Sep. 2, 2015 (EP) .................... 15183463

(51) Int. Cl.
*A61B 5/145* (2006.01)
*A61B 5/00* (2006.01)
(52) U.S. Cl.
CPC ........ *A61B 5/14546* (2013.01); *A61B 5/0002* (2013.01); *A61B 5/6847* (2013.01); *A61B 5/746* (2013.01)

(58) Field of Classification Search
CPC . A61B 5/14546; A61B 5/0002; A61B 5/6847; A61B 5/746; A61B 5/145;
(Continued)

(56) References Cited

U.S. PATENT DOCUMENTS

| 6,360,888 B1 | 3/2002 | McIvor et al. |
| 8,280,476 B2 | 10/2012 | Jina |

(Continued)

FOREIGN PATENT DOCUMENTS

| CN | 102473276 A | 5/2012 |
| CN | 104768450 A | 7/2015 |

(Continued)

OTHER PUBLICATIONS

International SearchReport dated Mar. 15, 2018, in Application No. PCT/EP2016/070645, 9 pages.

*Primary Examiner* — Eric F Winakur
*Assistant Examiner* — Abid A Mustansir
(74) *Attorney, Agent, or Firm* — Woodard, Emhardt, Henry, Reeves & Wagner, LLP

(57) ABSTRACT

A kit for determining a concentration of an analyte in a body fluid is disclosed, the kit comprising:
a) a sensor module comprising
  i. a sensor adapted to determine the concentration;
  ii. a control device connected to the sensor comprising a data collection device to collect measurement data acquired by the sensor, the control device further comprising a wireless near-field communication device adapted to transmit measurement data,
the sensor module comprising a sensor module mechanical interface;
b) a data reader module adapted to receive measurement data transmitted by the sensor module via wireless near-field communication, the data reader module comprising at least one data storage device;

(Continued)

c) a data transmission module to receive measurement data transmitted by the sensor module via wireless near-field communication, the data transmission module comprising a wireless far-field communication device to transmit the measurement data to an external device.

17 Claims, 9 Drawing Sheets

(58) Field of Classification Search
CPC . A61B 5/6833; A61B 5/0031; A61B 5/14532; A61B 2560/0412; A61B 2562/225
See application file for complete search history.

(56) References Cited

U.S. PATENT DOCUMENTS

| | | |
|---|---|---|
| 10,136,816 B2 | 11/2018 | Bernstein et al. |
| 2005/0199494 A1 | 9/2005 | Say et al. |
| 2008/0242962 A1* | 10/2008 | Roesicke ........... A61B 5/14546 600/347 |
| 2009/0112154 A1* | 4/2009 | Montgomery ..... A61B 5/14532 604/66 |
| 2009/0240128 A1 | 9/2009 | Mensinger et al. |
| 2010/0324392 A1 | 12/2010 | Yee et al. |
| 2011/0152644 A1 | 6/2011 | Heck et al. |
| 2011/0213225 A1* | 9/2011 | Bernstein ............... G06Q 50/22 600/309 |
| 2011/0273839 A1* | 11/2011 | Villegas ............... A61B 5/0002 361/679.41 |
| 2012/0022354 A1 | 1/2012 | Beyer et al. |
| 2012/0123227 A1 | 5/2012 | Sun et al. |
| 2012/0157801 A1 | 6/2012 | Hoss et al. |
| 2015/0045635 A1 | 2/2015 | Tankiewicz et al. |
| 2015/0182153 A1 | 7/2015 | Feldman et al. |
| 2015/0250422 A1 | 9/2015 | Bay |

FOREIGN PATENT DOCUMENTS

| | | |
|---|---|---|
| EP | 1 611 838 B1 | 10/2012 |
| EP | 1 850 226 A1 | 10/2015 |
| WO | WO 2003/005891 A1 | 1/2003 |
| WO | WO 2008/083379 A1 | 7/2008 |
| WO | WO 2008/124597 A1 | 10/2008 |
| WO | WO 2011/154372 A1 | 12/2011 |
| WO | WO 2012/007437 A1 | 1/2012 |
| WO | WO2012/068393 | 5/2012 |

* cited by examiner

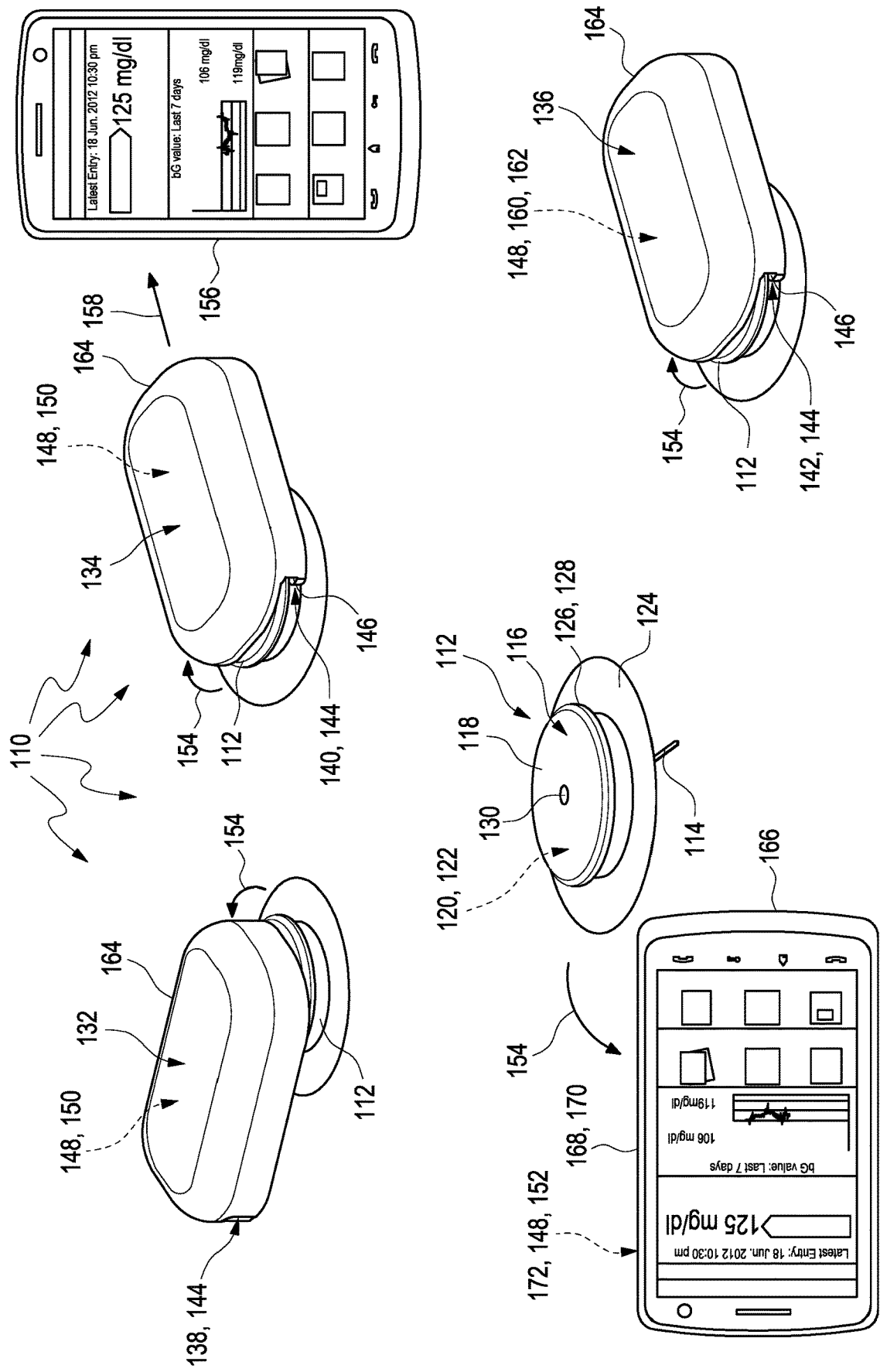

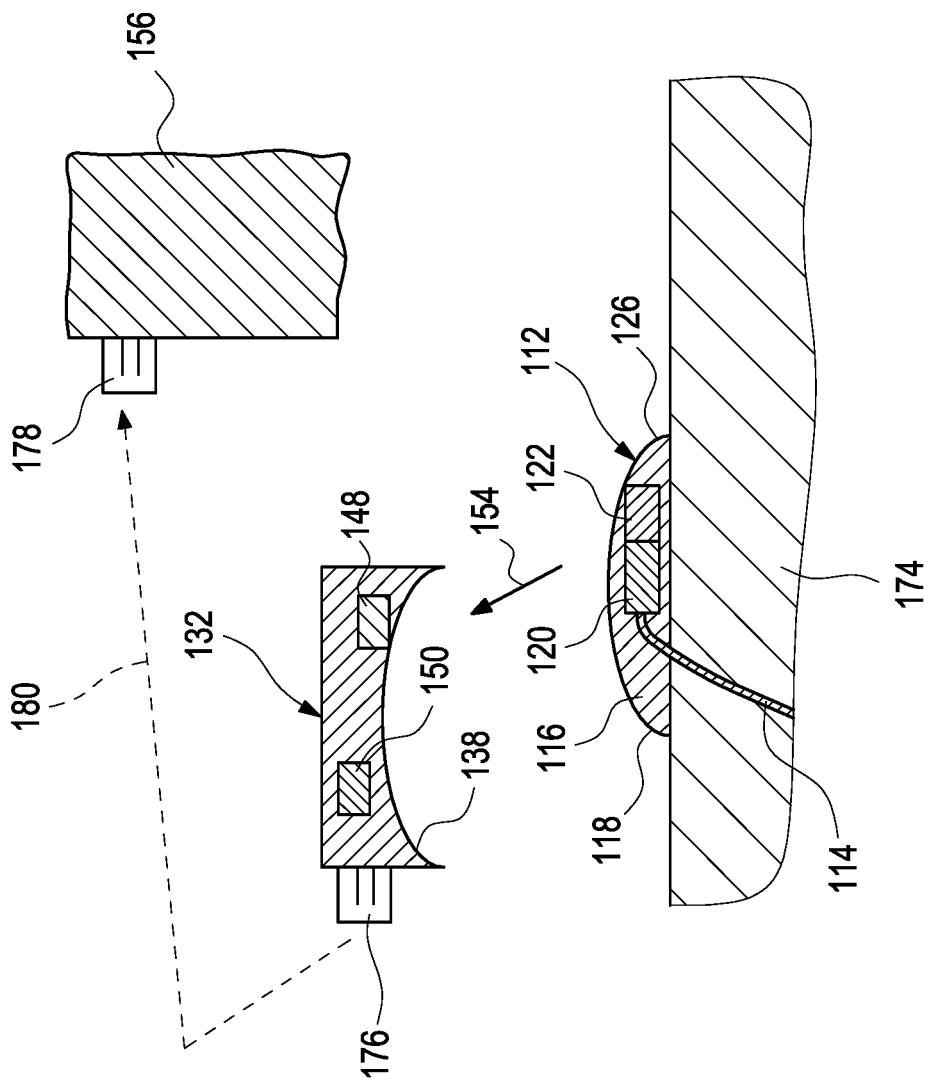

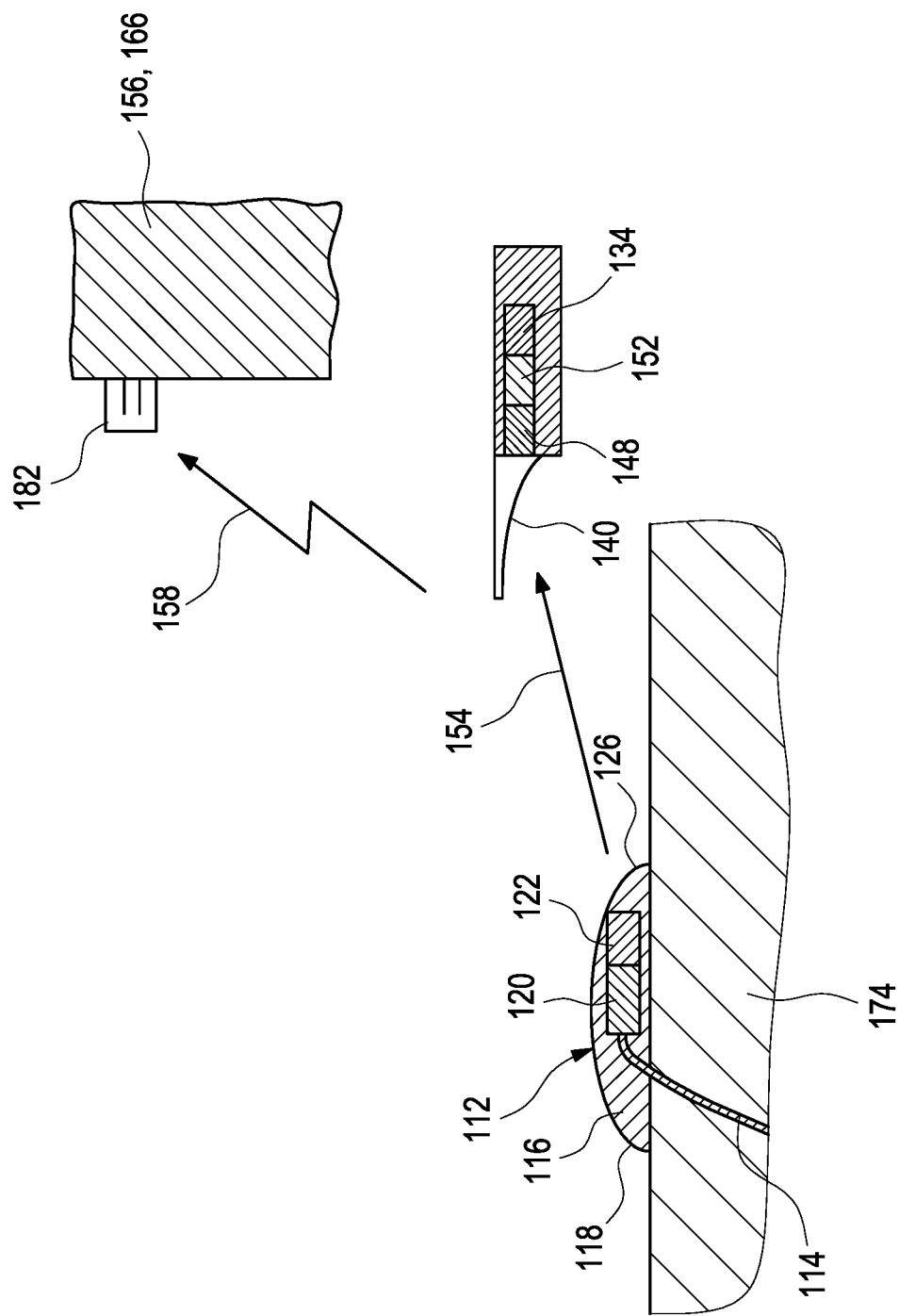

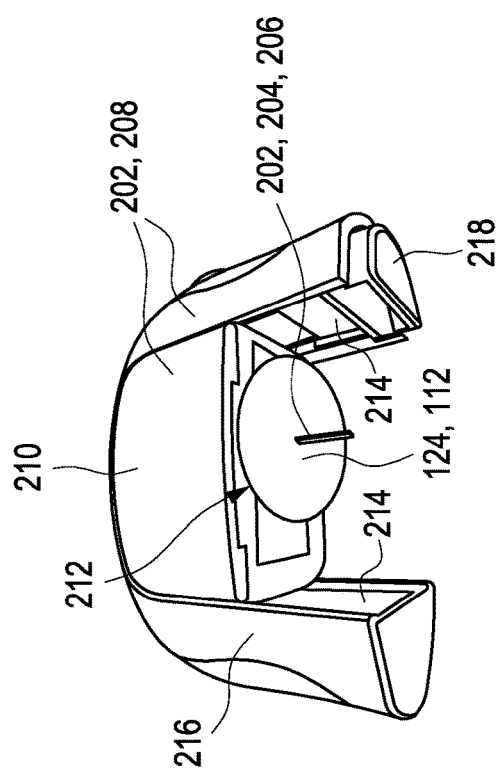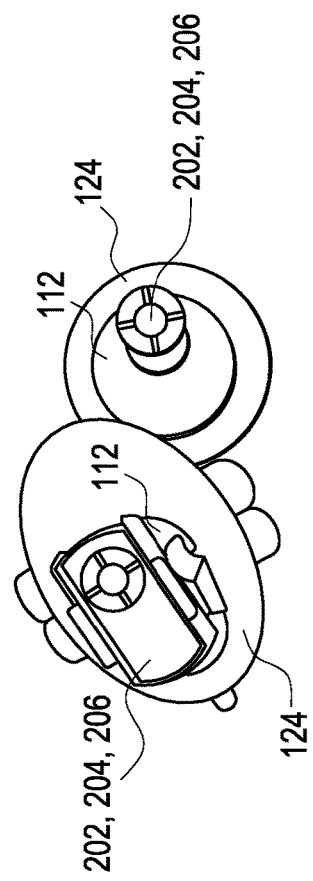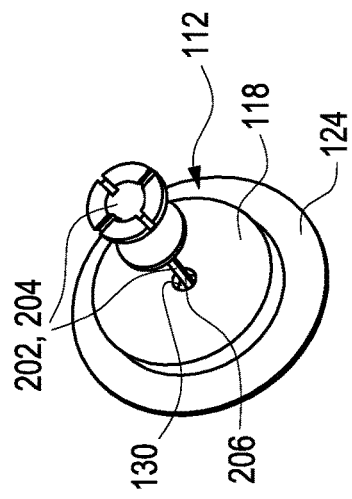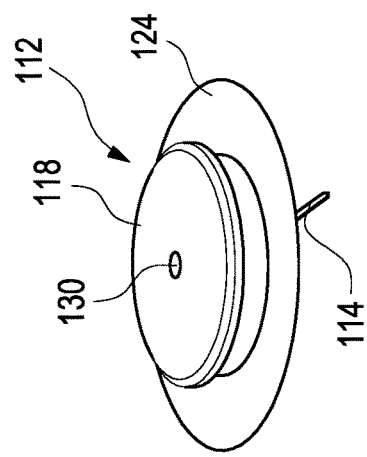

KIT FOR DETERMINING AN ANALYTE CONCENTRATION

FIELD OF THE INVENTION

The invention relates to a kit for determining a concentration of at least one analyte in a body fluid of a user. The invention further relates to a method for determining a concentration of at least one analyte in a body fluid of a user, the method comprising the use of the kit according to the present invention. Kits and methods according to the present invention are mainly used for long-term monitoring of an analyte concentration in a body fluid, such as for long-term monitoring of a blood glucose level or of the concentration of one or more other types of analytes in a body fluid. The invention may both be applied in the field of home care as well as in the field of professional care, such as in hospitals.

RELATED ART

Monitoring certain bodily functions, more particularly monitoring one or more concentrations of certain analytes, plays an important role in the prevention and treatment of various diseases. Without restricting further possible applications, the invention will be described in the following text with reference to blood-glucose monitoring. However, additionally or alternatively, the invention can also be applied to other types of analytes.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems are generally transcutaneous systems. This means that the actual sensor or at least a measuring portion of the sensor is arranged under the skin of the user. However, an evaluation and control part of the system (also referred to as a patch) is generally situated outside of the body of the user, that is to say outside of the human or animal body. In the process, the sensor is generally applied using an insertion instrument, which is likewise described in U.S. Pat. No. 6,360,888 B1 in an exemplary fashion. Other types of insertion instruments are also known.

WO 2008/124597 A1 discloses an analyte sensing device having one or more sensing electrodes. The analyte sensing device comprises a main body configured to reside on the skin of an individual when in use, the main body having one or more electrical components. The analyte sensing device further comprises an analyte sensing electrode extending substantially perpendicularly from and electrically coupled to the main body. The analyte sensing electrode is configured for insertion into the skin of the individual.

Transcutaneous sensor systems typically imply a large number of technical challenges. Thus, a first challenge resides in the fact that the lifetime of a sensor is limited. A sensor is generally worn for approximately one week. After that, influences such as enzymes being used up and/or a sealing off in the body generally reduce the sensitivity of the sensor, or it is expected that the sensor fails. Increasing the duration of wear is an area of current research. However, this means that the sensor and, optionally, components directly connected to the former such as an insertion needle, are often designed as replaceable components. Accordingly, the sensor and optionally further replaceable components generally constitute a so-called disposable. By contrast, in many cases, the evaluation and control part of the system is reused. Accordingly, this evaluation and control part is often embodied as a so-called reusable.

The separation between a disposable and a reusable, however, generally implies additional technical challenges. Thus, a significant challenge resides in the fact that the sensitive interface between the disposable part and the reusable part is susceptible to contamination, which might lead to deterioration of the quality of the electrical measurements. Further, electrochemical systems typically are based on a potentiostatic measurement principle and, generally, may sustain very small electrical currents only, since, with larger electrical currents, electrode deterioration may occur. The deterioration of measurement signals may occur gradually, over a long time period and may be detected electronically only with a large technical effort. These technical challenges are increased by the fact that the reusable part is generally handled by the end-user or patient rather than by trained medical staff.

US 2011/0152644 A1 discloses a protective container for holding a reusable control part of a transcutaneous sensor system for detecting at least one analyte in a bodily fluid. The control part includes at least one coupling, which has at least one sensor coupling for connection to at least one transcutaneous sensor. The protective container has at least one container housing. The control part can be held in the container housing. The container housing is adapted to shield the control part from environmental influences. The container housing also has at least one connector which can be connected to the coupling and seals the latter in a media-tight fashion.

A further challenge of continuous monitoring systems resides in the fact that these systems require a constant effort to keep the volume of the sensor system or at least the part of the sensor system worn on the user's body at a low level, in order to increase the comfort of wearing. Thus, the functionality of the sensor system generally has to be kept at a low level, in order to avoid voluminous components such as displays or user interfaces. This reduction of functionality, however, often leads to the fact that remote resources have to be used, such as for data evaluation and/or communication with the user. In this case, however, unidirectional or bidirectional exchange of data and information between the sensor and the remote device becomes an issue. Several systems for managing this communication are known in the art.

WO 2012/068393 A1 discloses an analyte monitoring system, comprising an on-body housing, an analyte sensor coupled to the housing, an electrical output interface disposed on an outer surface of the housing, and a removable adapter coupled to the housing. The removable adapter serves as a data conduit between the analyte sensor and a remote device.

US 2010/0324392 A1 discloses a sensor, comprising a body having a proximal section, a distal section longitudinally aligned with the proximal section and an intermediate section. The intermediate section is laterally displaced from at least the distal member, and a gap is defined between the laterally displaced intermediate section and a portion of the distal section.

WO 2012/007437 A1 discloses a medical device for carrying out at least one medical function. The medical device comprises at least one element that can at least partially be inserted into a body tissue of a user. The medical device further comprises a housing with a functional component that can be placed on the skin of a user.

WO 2011/154372 A1 discloses a medical device for detecting at least one analyte in a body fluid. The medical device comprises at least one implantable functional element, such as a sensor element, and at least one controller having at least one electronic component. The functional element can be connected to the controller. The controller comprises a housing having at least one metal housing. The controller comprises at least one wireless communication device. The metal housing comprises at least one slot structure. The communication device is designed to communicate with at least one external device, such as a data manager, by means of the slot structure.

WO 03/005891 A1 discloses a method of controlling data information between two portable medical apparatuses. Each apparatus has means for one or more of the following: storing, transmitting, receiving, processing and displaying data information. The two apparatuses have a number of interrelated positions during normal use. Via short-range communication, data information relevant to operations performed by the apparatuses is exchanged when the apparatuses are mutually positioned in one of a number of interrelated positions.

U.S. Pat. No. 8,280,476 B2 discloses a glucose monitor having a plurality of tissue piercing elements. Each tissue piercing element has a distal opening, a proximal opening and interior space extending between the openings. Further, a sensing area is provided in fluid communication with the proximal openings of the tissue piercing elements. Sensing fluid extending from the sensing area into substantially the entire interior space of the tissue piercing elements is provided. Further, a glucose sensor is provided, and adapted to detect a concentration of glucose in the sensing fluid within the sensing area.

EP 1 611 838 B1 discloses an analyte monitoring system, comprising a sensor implantable within tissue for monitoring continuously an analyte concentration. The sensor includes a signal transmitter configured to transmit a first wireless signal. The analyte monitoring system further comprises a handheld unit configured to receive the first wireless signal direct from the sensor and configured to measure the analyte concentration in an episodic manner using a disposable glucose test strip. The analyte monitoring system further comprises a signal relay configured to receive the first wireless signal direct from the sensor and to transmit a second wireless signal. The second wireless signal has a transmission range greater than the transmission range of the first wireless signal. The analyte monitoring system further comprises at least one signal receiver configured to receive the second wireless signal.

WO 2008/083379 A1 discloses a device, a system and a method for delivering a device such as a sensor or fluid transport structure or a fluid transport structure sensor combination into, for example, mammalian skin and receiving, analyzing and displaying signals from the device such as a sensor. The system includes a reusable sensor assembly including a transmitter, a microcontroller and a housing plus a disposable sensor assembly including a housing having an opening for receiving both the distal end of a biosensor, a sensor insertion guidance structure, and a transmission apparatus for transmitting signals received from the sensor to a reusable sensor assembly for transmission to an external electronic monitoring unit.

EP 1 850 226 A1 discloses apparatuses and methods to administer and manage a base unit for a handheld medical device. A base unit is in communication with a handheld medical device. The base unit is configured to provide an electrical connection to a power source to charge a battery of the handheld medical device. The base unit is also configured to perform an update to the operation of the base unit, wherein the update is initiated by the base unit upon receiving from the handheld medical device a data stream with information indicating that an update is contained in the data stream.

US 2005/0199494 A1 discloses an analyte sensor system. The analyte sensor system cornprises a sensor, a second control unit and a display unit. The sensor control unit is adapted to receive a portion of the electrochemical sensor and comprises a transmitter for transmitting data obtained by using the sensor to a display unit.

US 2009/0240128 A1 discloses a system for continuous measurement of an analyte in a host. The system includes a continuous analyte sensor configured to continuously measure a concentration of an analyte in a host and, further, a sensor electronics module physically connected to the continuous analyte sensor during sensor use. The sensor electronics module is configured to directly wirelessly communicate displayable sensor information to a plurality of different types of display devices.

Still, despite the progress that has been made with the above-mentioned concepts, some major technical problems and challenges remain. Thus, still, on the one hand, the volume of the body mount is an issue, since, specifically with increasing lifetimes of the actual sensor, the comfort of wearing the body mount in everyday life has to be increased. On the other hand, functionality of the sensor system has to be increased, specifically with regard to data management and evaluation, warning functions and interaction with other medical devices such as insulin pumps. Specifically, typical communication components allowing for a transfer of data and/or commands are rather voluminous. Further, flexibility of potential uses of the system has to be increased. Still, the requirements of increased comfort of wearing on the one hand and increased functionality and flexibility on the other hand are contradictory requirements and, thus, impose an increasing challenge on system design for continuous monitoring systems.

PROBLEM TO BE SOLVED

It is therefore an objective of the present invention to provide a concept for determination of a concentration of at least one analyte in a body fluid of a user which avoids the above-mentioned problems of known systems and devices and faces the contradictory requirements of a low volume and an increased functionality.

SUMMARY OF THE INVENTION

This problem is solved by a kit and a method with the features of the independent claims. Preferred embodiments, which might be realized in an isolated fashion or in any reasonable combination, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a kit for determining a concentration of at least one analyte in a body fluid of a user is disclosed.

As used herein, a "kit" is an assembly of a plurality of components, wherein the components each may function and may be handled independently from each other, wherein the components of the kit may interact to perform a common function. Thus, the kit may comprise a plurality of components, wherein each component may be handled individually, independent from the other components and may perform at least one function independently, wherein, further, all components or groups of components comprising at least two of the components may be combined, such as by physically connecting these components, in order to perform a common function implying functionality from the connected components.

As further used herein, the term "determining a concentration" relates to a process of generating at least one representative result or a plurality of representative results indicating the concentration of the analyte in the body fluid.

As further used herein, the term "analyte" may refer to an arbitrary element, component or compound which may be present in a body fluid and the concentration of which may be of interest for a user. Preferably, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be used and/or any combination of analytes may be determined.

Generally, an arbitrary type of body fluid may be used. Preferably, the body fluid is a body fluid which is present in a body tissue of the user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the concentration of the at least one analyte in the body fluid of the user may preferably be determined in vivo.

As generally used within the present invention, the term "user" may refer to a human being or an animal, independent from the fact that the human being or animal, respectively, may be in a healthy condition or may suffer from one or more diseases. As an example, the user may be a human being or an animal suffering from diabetes. However, additionally or alternatively, the invention may be applied to other types of users.

The kit comprises the following components. As outlined above, these components may be handled independently from each other, i.e. each of the components may have at least one state in which the respective component is not mechanically connected to any other component. Additionally, as will be outlined in further detail below, the components of the kit have at least one state in which these components are mechanically connected to at least one other component, thereby mechanically interacting with this component. Further, each of the components of the kit may have an individual function, such as a measurement function, a data storage function and a data transmission function, which may be exerted independently from the presence of other components. Further, in the connected state, an interaction function may occur, which will be outlined in further detail below.

Firstly, the kit comprises at least one sensor module. The sensor module comprises at least one sensor element adapted to determine the concentration of the analyte, wherein the sensor element is at least partly implantable into a body tissue of the user. The sensor module further comprises at least one control device connected to the sensor element, wherein the control device comprises at least one data collection device adapted to collect measurement data acquired by using the sensor element. The control device further comprises at least one wireless near-field communication device adapted to transmit measurement data.

As used herein, the term "sensor module" generally refers to a unit, which may be handled as one entity, comprising the at least one sensor element, preferably precisely one sensor element, and the at least one control device, preferably precisely one control device.

As further used herein, the term "sensor element" generally refers to an arbitrary element which is adapted to determine the concentration of the analyte. Thus, as will be outlined in further detail below, the at least one sensor element preferably comprises at least one sensor material, wherein the sensor material is adapted to perform at least one detectable reaction in the presence of the analyte. The sensor material preferably may be a sensor material selected from the group consisting of: an optical sensor material, wherein the optical sensor material is adapted to perform at least one optically detectable detection reaction in the presence of the analyte; an electrochemical sensor material, wherein the electrochemical sensor material is adapted to perform at least one electrically detectable detection reaction in the presence of the analyte, such as an electrically detectable redox reaction.

The sensor element preferably may comprise at least one flexible substrate, such as a flexible substrate having an elongated shape, wherein the flexible substrate may extend into the body tissue of the user. Specifically in case the at least one sensor element is an electrochemical sensor element, the sensor element preferably has two or more electrodes applied to the substrate, such as at least one working electrode and at least one further electrode, such as at least one counter electrode and/or at least one reference electrode.

For potential examples of the sensor element, reference may be made to the prior art documents listed above, such as to the continuous transcutaneous measurement systems as described in U.S. Pat. No. 6,360,888 B1 or in US 2008/0242962 A1. Additionally or alternatively, other types of sensor elements may be used.

As further used herein, the term "at least partly implantable into a body tissue of the user" refers to the fact that the sensor element is adapted to have appropriate dimensions to be inserted into the body tissue of the user, such as into subcutaneous tissue, and, further, that the sensor element is biocompatible in order to remain in the body tissue for an elongated time period, such as for several days or even several weeks or several months. Thus, as an example, the sensor element or at least the implantable part of the sensor element may have a biocompatible coating, such as at least one semipermeable membrane, which prevents the sensor material from migrating into the body tissue and, still, which is permeable to the at least one analyte. Thus, as outlined above, the sensor element may comprise at least one flexible substrate with two or more electrodes deposited on the substrate, wherein at least one of the electrodes is coated by a semipermeable membrane. Thus, the electrodes each may comprise a conductive electrode pad, wherein at least one of these electrode pads is coated with the sensor material, functioning as a working electrode. The conductive electrode pads may be contacted by two or more contact leads.

The term "implant" refers to the fact that the sensor element may be inserted fully or partially into the body tissue. Thus, in the following, the terms "implant" and "insert" will be used as synonyms. Generally, during implantation and/or during use of the sensor element, the sensor element may fully or partially penetrate the skin of the user. Thus, the sensor element preferably may be embodied as a transcutaneous sensor element.

As used herein, the term "control device" generally refers to an arbitrary element which is adapted to acquire measurement data by using the data collection device. The control device preferably may rest on a skin surface of the user, wherein the sensor element preferably extends from the control device into the body tissue of the user. The control device preferably may have a closed housing, as will be outlined in further detail below. The data collection device preferably may have at least one electronic component connected to the sensor element, preferably electrically connected to the sensor element. As will be outlined in further detail below, the connection may be a permanent connection or a releasable and/or reversible connection.

Preferably, specifically in case the sensor element is an electrochemical sensor element, the data collection device may comprise at least one potentiostatic measurement device such as at least one potentiostat. Generally, the data collection device may comprise at least one amplifier having a high input resistance, such as an input resistance of at least 1 MΩ, preferably at least 100 MΩ or even at least 1 GΩ, such as 10 GΩ. Generally, for potential embodiments of the control device and the data collection device, reference may be made to the electronics measurement setups as disclosed in U.S. Pat. No. 6,360,888 B1 or in US 2008/0242962 A1. However, as will be outlined in further detail below, the at least one control device preferably is a unitary control device which is not subdivided into a reusable and a disposable part. Apart from this fact, the measurement setups as disclosed in these documents may be transferred to the present invention. Other embodiments are feasible.

As further used within the present invention, the term "measurement data" refers to arbitrary data acquired by using the sensor element, indicative of the analyte concentration. The measurement data may specifically comprise a plurality of measurement values acquired at subsequent points in time, such as over a time period of several hours, several days, several weeks or even several months. The measurement data preferably may be acquired in an analogue or digital electronic format. The measurement data further may be processed or pre-processed within the control device, such as by applying at least one evaluation or pre-evaluation algorithm to the measurement data. Thus, as an example, at least one algorithm may be applied to the measurement data, wherein the at least one algorithm transforms primary measurement data acquired by using the sensor element into secondary measurement data indicating the concentration of the analyte in the body fluid, such as by applying a known or predetermined relationship between the primary measurement data and the analyte concentration to the primary measurement data, thereby generating secondary measurement data. Here and in the following, no difference will be made between primary measurement data, i.e. the measurement data directly acquired by using the sensor element, and secondary measurement data which are generated by applying one or more evaluation or pre-evaluation algorithms to the primary measurement data.

As used herein, the term "near-field communication", abbreviated by NFC, generally refers to a wireless transfer of data over short distances of up to 10 cm, generally having a low data transfer rate, such as a data transfer rate of no more than 424 kBit/s. As an example, the near-field communication may follow a passive standard, i.e. a standard in which one of the communication partners is a passive component which only answers communication requests received from the other partner, such as the standard defined in ISO 14443 and/or ISO 15693. Thus, preferably, the near-field communication may be a RFID communication, wherein, preferably, the wireless near-field communication device of the control device is the passive element of the RFID communication. Additionally or alternatively, other types of near-field communication may be used, such as near-field communications in which both partners of the communication are active partners, i.e. partners which may both send and receive communication requests.

The near-field communication device preferably may comprise at least one communication component adapted to perform the near-field communication. Thus, as an example, the near-field communication device may comprise at least one antenna. As an example, the near-field communication device may comprise at least one RFID antenna, such as at least one RFID coil.

The transmission of the measurement data by using the wireless near-field communication device may take place to one or more other elements, such as one or more other elements of the kit, as will be outlined in further detail below. Thus, the communication of the measurement data by using near-field communication may take place to one or more of the data reader module, the data transmission module, the optional alarm module and the portable data management device, which will be explained in further detail below.

The sensor module further comprises a sensor module mechanical interface. As used herein, the term "sensor module mechanical interface" generally refers to an arbitrary element or a combination of elements of the sensor module which is adapted to interact with at least one mechanical interface of a second element in order to generate a mechanical connection between the sensor module and the other element. As will be outlined in further detail below, the other element preferably may be selected from the group consisting of the data reader module, the data transmission module, the optional alarm module and the optional portable data management device. Generally, the sensor module mechanical interface may comprise an arbitrary type of element or combination of elements which may be used for coupling to the other element, such as one or more elements selected from the group consisting of: a protrusion, a rim, a hook, a depression, a groove. Other types of connection elements may be used additionally or alternatively.

The kit further comprises at least one data reader module adapted to receive measurement data transmitted by the sensor module via wireless near-field communication. The data reader module comprises at least one data storage device and is adapted to store the measurement data.

As used herein, the term "data reader module" generally refers to a unit which may be handled as a unitary element and which is adapted to store the measurement data. For the purpose of receiving measurement data transmitted by the sensor module via wireless near-field communication, the data reader module may comprise at least one near-field communication device. Thus, as an example, a near-field communication device according to one or more of the above-mentioned standards may be used. As an example, the near-field communication device of the data reader module may be an active device, whereas the wireless near-field communication device of the control device of the sensor module may be a passive communication device. However, other options are possible, such as active communication devices in both components. The near-field communication device of the data reader module preferably may comprise at least one antenna, such as at least one RFID antenna.

The data storage device may be an arbitrary storage device adapted to store the measurement data. A volatile and/or non-volatile data storage device may be used. As an example, the storage device, also referred to as a memory device or a memory element, may comprise one or more storage chips and/or other types of memory devices, wherein both volatile and non-volatile memory devices may be employed.

The kit further comprises at least one data transmission module adapted to receive measurement data transmitted by the sensor module via wireless near-field communication. The data transmission module comprises at least one wireless far-field communication device, wherein the wireless far-field communication device is adapted to transmit at least part of the measurement data to an external device via wireless far-field communication.

As used herein, the term "data transmission module" generally refers to an arbitrary unit which may be handled as a unitary element which is adapted to receive the measurement data via wireless near-field communication from the sensor module and which is adapted to transmit at least part of the measurement data to an external device via wireless far-field communication. Thus, the data transmission module may comprise at least one wireless near-field communication device adapted to communicate with the wireless near-field communication device of the control device of the sensor module. As an example, the near-field communication device may be an active near-field communication device, whereas the near-field communication device of the control device of the sensor module may be a passive communication device. However, other options are possible, such as active communication devices in both elements.

As used herein, the term "wireless far-field communication" generally refers to a wireless communication adapted to transmit data over long distances, such as distances of more than 10 cm. As an example, the wireless far-field communication may be an arbitrary long-range communication using electromagnetic waves in the radio frequency range, i.e. may be a radio communication. Thus, as an example, the wireless far-field communication device of the data transmission module may comprise at least one radio module, having at least one radio antenna, for transmitting the measurement data via radio transmission to the at least one external device.

As used herein, the term "external device" may be an arbitrary device independent from the data transmission module and the sensor module which is adapted to receive the measurement data via wireless far-field communication. The at least one external device may be part of the kit or may be independent from the kit. As an example, the at least one external device may be a portable device having the capability of communicating via wireless far-field communication, such as a hand-held computer and/or a smartphone. Other examples are feasible.

The data reader module and the data transmission module each comprise a mechanical interface adapted to reversibly engage the sensor module mechanical interface. Thus, the data reader module may comprise a data reader module mechanical interface, and the data to transmission module may comprise a data transmission module mechanical interface. As used herein, the term "engage" generally refers to the fact that the mechanical interface of the data reader module or the data transmission module, respectively, may mechanically interact with the sensor module mechanical interface, such as by mechanical cooperation. The term "reversibly" generally refers to the fact that the interaction may be a detachable interaction, which, by appropriate handling, may be detached. Generally, the mechanical interfaces of the data reader module and the data transmission module are adapted to alternatively generate a fixed spatial relationship between the sensor module and the data reader module or the sensor module and the data transmission module. Thus, in a first alternative, the data reader module mechanical interface may engage the sensor module mechanical interface, thereby generating a fixed spatial relationship between the sensor module and the data reader module. Thus, in this first alternative, the sensor module and the data reader module are connected. In a second alternative, the data transmission module mechanical interface may engage the sensor module mechanical interface, thereby generating a fixed spatial relationship between the sensor module and the data transmission module. Thus, in this second alternative, the sensor module may be connected to the data transmission module. In the first alternative, the data transmission module may be disconnected from the sensor module, and in the second alternative, the data reader module may be disconnected from the sensor module.

As used herein, the term "fixed spatial relationship" generally may refer to the fact that, in a connected state, the connected components, such as the sensor module and the data reader module or the sensor module and the data transmission module, form a connected unit comprising the two components in a predetermined orientation and/or distance. Preferably, the sensor module mechanical interface and the data reader module mechanical interface or the data transmission module mechanical interface may be adapted to form a form-fit or force-fit connection.

The data reader module and/or the data transmission module, and, optionally, one or more further modules such as the optional alarm module as explained in further detail below, in addition to being held in a fixed spatial relationship by the mechanical interface, may further be attached to the user's body by one or more attachment elements. Thus, one or more of these modules may additionally be attached to the user's body by an adhesive tape and/or a Velcro fastener. Thus, by using one or more additional attachment elements, the mechanical stability, in a coupled state, may additionally be increased.

By using the data reader module and the data transmission module as separate components, the functionality of the kit may be extended as compared to a single sensor module, wherein, still, the volume and resources required within the sensor module may be kept at a minimum. Alternatively, the data reader module and the data transmission module may be coupled to the sensor module. Thus, the configuration of the kit and the coupling of the components of the kit may be adapted to the actual needs of the measurement situation. Thus, in a first state, such as a state during everyday use, the sensor module may be disconnected from the data reader module and from the data transmission module, thereby providing a maximum comfort to the user, since the weight and the volume of the sensor module may be kept at a low level. Thus, the sensor module may have a volume below 7 $cm^3$, more preferably a volume below 5 $cm^3$, below 2.5 $cm^3$, or even below 2 $cm^3$ or below 1.5 $cm^3$. Specifically, the sensor module and, more preferably, the control device of the sensor module, may be embodied such that no voluminous components are present, such as voluminous wireless far-field communication components and/or voluminous data memories. Further, the sensor module may be embodied without any wire-bound data interfaces, such as without any mechanical plugs. Consequently, the sensor module may be embodied as a cheap, small, low-level component which simply may be adapted to acquire measurement data and transmit the measurement data via wireless near-field communication. Additionally, however, the sensor module may comprise other components, such as data storage devices (memories), preferably at a low level. Further, the sensor module may comprise at least one energy storage, as will be outlined in further detail below.

Still, despite the fact that the sensor module may be kept at a low resource level and, thus, at a low level with regard to weight and volume, the kit may provide a full functionality of modern analytical systems, such as by providing the capability of far-field data transmission to data handling devices such as one or more computers for evaluating the measurement data. Further, the data reader module may be used for data storage and/or data transfer, in the fashion of modern memory sticks, such as USB memory sticks.

The kit may further comprise additional components. Thus, as an example, the kit may further comprise at least one alarm module adapted to receive data transmitted by the sensor module via wireless near-field communication. The data transmitted by the sensor module may contain one or both of the measurement data or alarm instructions. The alarm module may be adapted to generate at least one alarm signal in response to the data transmitted by the sensor module.

Thus, as an example, the alarm module may comprise at least one wireless near-field communication device, preferably an active near-field communication device, which may communicate with the near-field communication device of the control device of the sensor element. As an example, the wireless near-field communication device may comprise at least one antenna.

As outlined above, the data transmitted by the sensor module may contain alarm instructions. Thus, the alarm module may be a passive alarm module which simply is adapted for generating an alarm signal in response to alarm instructions received by the sensor module. Thus, the sensor module may be adapted to determine whether at least one alarm condition is fulfilled, such as in case one or more thresholds of analyte concentration are exceeded, and, if this is the case, may transmit alarm instructions to the alarm module. The alarm module may generate an alarm signal in response to these alarm instructions.

Additionally or alternatively, the alarm module may provide, at least to a certain extent, an intelligence of its own, such as by providing one or more processors or other types of data processing devices. Thus, as outlined above, the data transmitted by the sensor module may contain measurement data. The alarm module may be adapted to evaluate the measurement data and to determine whether at least one alarm condition is fulfilled and to provide at least one alarm signal in case the at least one alarm condition is fulfilled. Thus, the alarm module may comprise at least one data processing device, such as at least one processor and/or microcontroller, adapted to perform at least one evaluation algorithm, wherein the evaluation algorithm is adapted to evaluate the measurement data received by the sensor module and to determine whether the alarm condition is fulfilled or not. Thus, as an example, the at least one alarm condition may comprise at least one comparison with one or more threshold levels, wherein, as an example, an alarm condition may be fulfilled in case a specific threshold level is reached and/or exceeded. Thus, as an example, an alarm condition may be fulfilled in case a maximum tolerable blood glucose level is exceeded. The alarm module may be flexible with regard to evaluating the measurement data. Thus, the alarm module may be a programmable alarm module. As an example, a user may select and/or adjust one or more thresholds to be used in the alarm condition, such as one or more thresholds for analyte concentrations. For this purpose, such as for programming the alarm module, the alarm module may comprise one or more wireless and/or wire bound interfaces, such as one or more interfaces adapted to be connected to a personal computer, a smartphone or another type of controller. Via one or more of these interfaces, a programming of the alarm module may be feasible.

The at least one alarm signal, as outlined in further detail below, may be generated by at least one alarm device. The at least one alarm signal preferably may be selected from the group consisting of an acoustic alarm signal, an optical alarm signal and a vibrational alarm signal. However, other types of alarm signals may be generated, such as alarm signals transmitted via wireless or wire-bound data transmission to at least one external device, such as to at least one medical computer.

The alarm module comprises at least one mechanical interface adapted to reversibly engage the sensor module mechanical interface, as an alternative to the data reader module and the data transmission module. The mechanical interface of the alarm module may also be referred to as the alarm module mechanical interface. For potential embodiments of the alarm module mechanical interface, reference may be made to the embodiments of the data reader module mechanical interface and/or the data transmission module mechanical interface as outlined above. Thus, as a third alternative, the alarm module may be coupled to the sensor module, wherein, preferably, in this third alternative, the data reader module and the data transmission module are detached from the sensor module. The alarm module mechanical interface may reversibly engage the sensor module mechanical interface, thereby generating a fixed spatial relationship between the sensor module and the alarm module. As outlined above, additionally, the alarm module may be attached to the user's body by one or more attachment elements, such as one or more of an adhesive tape or a Velcro fastener.

As outlined above, the alarm module preferably may comprise at least one data evaluation device, also referred to as a data processing element. Preferably, the at least one data processing element may have a software code stored therein, with program means for subjecting the measurement data to the at least one alarm condition. Thus, by using the program means, the above-mentioned threshold comparisons may be performed. Additionally or alternatively, as outlined above, the alarm module simply may be a passive alarm module adapted for receiving one or more alarm instructions from the sensor module and to provide an alarm signal in response to this at least one alarm instruction.

As outlined above, the alarm signal preferably may be selected from the group consisting of an acoustic alarm signal, an optical alarm signal and a vibrational alarm signal. However, additionally or alternatively, other types of alarm signals may be generated, such as one or more electronic alarm signals, e.g. alarm signals transmitted via wire-bound and/or wireless signal transmission, such as radio-transmission, to an external device, such as an external computer and/or a smartphone. Thus, generally, the alarm signal may be an alarm signal which may be recognized by a human user, such as healthcare personal or the user of the kit, and/or an electronic alarm signal which may be recognized as such by a machine.

Additionally or alternatively to the at least one alarm module, the kit may further comprise at least one portable data management device. The portable data management device may be adapted to directly or indirectly receive the measurement data and to at least partially display the measurement data. As used herein, the term at least partially display generally refers to the fact that one or more of the full measurement data, a part thereof or data or information derived from the measurement data are displayed by using at least one display device, such as a matrix display. As an example, measurement curves derived from the measurement data may be displayed on a screen, such as LCD screen or any other type of display device.

The portable data management device may further be adapted to perform at least one data evaluation algorithm. Thus, the portable data management device may further be adapted to apply the at least one data evaluation algorithm on the measurement data or a part thereof, such as in order to derive at least one evaluation result. As an example, an analyte concentration, mean values, a health condition or other types of evaluation results may be derived by using the evaluation algorithm.

Thus, generally, the data management device may simply be a display device adapted for displaying data, only, whereas the sensor module and/or the data transmission module may provide the capability of data evaluation. Alternatively, the data management device may provide an intelligence of its own, such as by providing one or more data processing devices adapted to apply the at least one data evaluation algorithm on the measurement data.

As used herein, the term "portable" generally refers to the fact that the data management device may be carried by a user, such as by hand. Thus, the data management device may be a hand-held data management device. As an example, the data management device may have a weight of less than 1 kg, preferably a weight of less than 500 g and, more preferably, a weight of less than 300 g. Further, the portable data management device may have a volume of preferably less than 1000 $cm^3$, more preferably of less than 120 $cm^3$ or even less than 60 $cm^3$.

Generally, the term "data management device", as used herein, refers to a device adapted to handle measurement data, such as by storing the measurement data and/or subjecting the measurement data to at least one data evaluation algorithm. Thus, as an example, the data management device may have at least one algorithm for displaying the measurement data, such as by displaying the measurement data on a display device, thereby displaying one or more measurement curves. Additionally or alternatively, averaging algorithms may be applied to the measurement data and/or one or more algorithms adapted to give medical advice to the user. Further, the portable data management device may comprise one or more databases, such as for storing and/or comparing measurement data.

The portable data management device may be adapted to directly or indirectly receive the measurement data. As used herein, the term "directly receiving the measurement data" refers to the option that the portable data management device directly receives the measurement data from the sensor module, such as by wireless near-field communication. The term "indirectly receiving the measurement data" generally refers to the option that at least one intermediate device may be used for transmitting the measurement data fully or in part to the portable data measurement device. Thus, the at least one data transmission module may be used for transmitting the measurement data fully or in part to the portable data management device via wireless far-field communication. These options will be outlined in further detail below.

In addition to displaying the measurement data and, optionally, applying at least one evaluation algorithm to the measurement data, the data management device may further be adapted to perform one or more additional actions. Thus, as an example, the data management device may be adapted to initiate one or more further actions, such as to automatically shut off a medication pump, specifically an insulin pump, in response to the measurement data. Thus, as an example, the data evaluation algorithm may be adapted to determine whether one or more conditions are fulfilled, on the basis of the measurement data, and, in response to this determination, may initiate one or more actions such as shutting off the medication pump.

Further, the data management device may be adapted to send data and/or instructions to one or more other devices. Thus, as an example, the data management device may be adapted to communicate with the sensor module. As an example, the data management device may be adapted to transmit data to the sensor module, preferably via near-field communication. As an example, the data management device may be adapted to transmit calibration data to the sensor module. Additionally or alternatively, the data management device may be adapted to transmit specific alarm conditions and/or alarm adjustments which may individually be adjustable by a user.

The portable data management device may comprise at least one device selected from the group consisting of: a portable computer; a smartphone; a watch; a medication pump, such as an insulin pump or a part thereof, such as a medication pump controller; a hand-held device for determining a concentration of the analyte in a body fluid. In case the portable data management device comprises a hand-held device for determining a concentration of the analyte in a body fluid, the hand-held device generally may comprise an arbitrary meter for determining the analyte concentration. Thus, as an example, the hand-held device may be adapted to use at least one test element having at least one test field, preferably a test strip or a test tape, wherein a sample of the body fluid may be applicable to the test field. Thus, as opposed to the implantable sensor element of the sensor module, the hand-held device may be a spot meter adapted to perform an in vitro analysis of the body fluid. Thus, as an example, the hand-held device may be a hand-held glucose monitoring device using one or more test strips or one or more test tapes, wherein a sample of the body fluid, such as a droplet of blood and/or interstitial fluid, may be applied to the test strip or test tape, in order to determine the concentration of the analyte in the body fluid, such as the blood glucose concentration. Thus, the hand-held device generally may comprise a commercially available blood glucose meter. Additionally or alternatively, other types of hand-held devices for determining the analyte concentration may be used.

The data management device further may comprise one or more user interfaces allowing for a user to insert commands. Thus, the data management device may comprise one or more keys for inserting data and/or commands. The data management device additionally or alternatively may comprise at least one data processing element adapted to apply at least one data processing algorithm to the measurement data. Thus, the data processing element may be adapted to apply at least one averaging algorithm and/or at least one evaluation algorithm to the measurement data, wherein, as an example, one or more types of information may be derived from the measurement data, such as information regarding the measurement data exceeding certain levels of the analyte concentration. Further, additionally or alternatively, the data management device may comprise one or more databases for storing the measurement data.

The measurement device may be adapted to receive measurement data from the data transmission module via wireless far-field communication. Thus, as an example, the data management device may comprise one or more far-field communication components, such as one or more radio components. Additionally or alternatively, the data management device may be adapted to receive measurement data from the data transmission module via other ways of communication.

The data management device further may be adapted to receive measurement data directly from the sensor module via wireless near-field communication. Thus, the data management device may comprise one or more wireless near-field communication devices. Thus, as an example, many hand-held devices such as modern smartphones comprise near-field communication devices, such as for reading RFID tags. Thus, as an example, the data management device may comprise one or more RFID readers to receive measurement data via RFID communication from the sensor module.

The data management device may further comprise at least one display element adapted to display a plurality of measurement data. Thus, the display element may comprise an active or passive display, such as a matrix display. Thus, the display element may be adapted to display measurement curves comprising a plurality of measurement data. Thus, the measurement device may be adapted to display a time development of the measurement data.

Further preferred embodiments relate to the control device. Thus, as outlined above, the control device preferably may comprise at least one energy storage. Thus, the control device may comprise at least one battery and/or at least one accumulator. Other types of energy storage devices may be used. The energy storage device may be a rechargeable or a non-rechargeable energy storage device.

The control device further may comprise at least one data storage, such as at least one data memory. Thus, the control device may comprise one or more non-volatile or volatile data memories. As outlined above, however, the data storage device of the control device preferably may be kept a low level, such as for intermediate storage of the measurement data.

The wireless near-field communication device of the control device preferably, as outlined above, may comprise at least one antenna. Thus, the near-field communication device of the control device may comprise at least one inductance or inductivity, such as at least one coil, for inductive coupling of signals. As outlined above, the wireless near-field communication may comprise an active near-field communication or a passive near-field communication, from the point of view of the near-field communication device of the control device of the sensor module. Thus, the near-field communication, as an example, may be an RFID communication, wherein the wireless near-field communication device of the control device of the sensor module may be an active device or a passive device.

In case the wireless near-field communication device comprises one or more inductances or inductivities such as one or more coils, these elements may also be used for providing energy. Thus, as an example, energy may be transferred by inductive coupling, such as energy which may be used by the control device.

The wireless far-field communication device of the data transmission module, as outlined above, may be adapted to perform a radio transmission. Thus, as an example, the wireless far-field communication device of the data transmission module may comprise at least one radio transmitter.

The data reader module may comprise one or more interfaces adapted to at least partially transfer the measurement data to an external device. Thus, as an example, the interface may comprise a wire-bound interface, such as an electrical plug for data transmission. As an example, the wire-bound interface may comprise a USB interface. However, additionally or alternatively, other types of wire-bound interfaces may be used.

The interface preferably may be selected from the group consisting of a USB interface, an infrared interface and a Bluetooth interface. However, additionally or alternatively, other types of interfaces may be used.

By providing this at least one interface, the data reader module may be used as a data stick. The data reader module preferably may have a volume of less than 20 $cm^3$, preferably of less than 15 $cm^3$, more preferably of less than 10 $cm^3$ or even less than 7 $cm^3$. Thus, the data reader module may be used as a data transfer stick, allowing for intermediate storage of measurement data. The measurement data may be evaluated at a later point in time, such as by connecting the data reader module to at least one computer, such as by using the at least one wire-bound interface and/or the wireless interface of the data reader module. Thus, similar to the way a USB stick is used, the data reader module may comprise a USB plug which may be plugged into a port of a computer, in order to transfer the measurement data to a computer, for evaluation purposes and/or database purposes. The data reader module may further comprise one or more data evaluation algorithms stored thereon which may be transferred to the computer in order to allow for the computer to evaluate the measurement data. As an example, the data reader module may comprise one or more self extracting software programs for evaluating the measurement data, such as for evaluating continuous glucose monitoring data. The latter generally provides the advantage that no preinstalled software on the computer is required, such that the user may evaluate or inspect the measurement data on an arbitrary computer.

Further preferred embodiments refer to the control device. Thus, generally, the control device may comprise a closed housing. As used herein, the term "closed" refers to the fact that the housing may comprise a tight enclosure against moisture and/or dirt. The closed housing, preferably, may be a unitary housing which may not be disassembled into separate components of the housing without destroying the housing, i.e. which may not be reversibly separated into housing parts. As an example, the closed housing may be made of a closed plastic material. As an example, a thermoplastic and/or elastomeric material may be used. The closed housing preferably may be made of a unitary piece of material, such as by using a molding process.

The sensor module mechanical interface may be part of the at least one housing and/or may be attached to the at least one housing of the sensor module. Thus, the sensor module mechanical interface may comprise at least one protrusion formed on an outer side of the housing. The protrusion may comprise a protruding rim, such as a circumferential protruding rim. The protrusion may provide a simple, fast and reliable mechanical attachment. Still, a large number of other geometric embodiments of the mechanical interface are feasible.

The housing may comprise one or more openings through which an insertion tool for into setting the sensor element into the body tissue may penetrate the housing, i.e. may be led through the housing. Thus, the housing may comprise one or more through-holes. As an example, at least one opening may be provided, wherein the opening specifically may be selected from the group consisting of: a through-hole penetrating the housing along an axis of symmetry; an offset through-hole penetrating the housing offside an axis of symmetry; an oblique through-hole penetrating the housing along an axis of penetration, the axis of penetration forming an angle $\alpha$ with an axis of symmetry of the housing, wherein $0°<\alpha<90°$, preferably $20°<\alpha<70°$, more preferably $\alpha=45°$. As an example, the at least one opening may be a central opening within the housing of the sensor module. The opening may be a through-hole penetrating the housing along an axis of symmetry. Additionally or alternatively, other embodiments are feasible.

The kit may further comprise at least one insertion device, the insertion device comprising at least one skin-penetration element adapted to perforate the skin of the user and to guide the sensor element into the body tissue of the user. Thus, the skin-penetration element may comprise at least one cannula. Thus, the cannula may be a needle having a central lumen for receiving the sensor element during insertion. Preferably, the cannula is a slotted cannula. The insertion device may further comprise at least one driving mechanism for driving the skin-penetration element, such as the at least one cannula, into the body tissue. The driving mechanism, as an example, may comprise at least one actuator adapted for forcefully moving the skin-penetration element through the skin into the body tissue. Thus, as an example, the driving mechanism may comprise at least one spring-based driving mechanism, adapted for transforming a mechanical energy stored in one or more springs into a movement of the skin-penetration element. Driving mechanisms of this fashion are generally known in the art, such as from U.S. Pat. No. 6,360,888 B1. Thus, for specific details of the embodiment of the driving mechanism, reference may be made to this document. However, additionally or alternatively, other types of driving mechanisms may be used.

The insertion device preferably may comprise at least one mechanical interface adapted to engage the sensor module mechanical interface during insertion of the sensor element. Thus, the insertion device may comprise at least one insertion device mechanical interface. The insertion device mechanical interface generally may be embodied in a similar way to the data reader module mechanical interface and/or the data transmission module mechanical interface. Thus, the insertion device mechanical interface may be adapted to reversibly engage the sensor module mechanical interface, thereby generating a fixed spatial relationship between the sensor module and the insertion device during insertion of the sensor element into the body tissue.

Further preferred embodiments may refer to the connection between the sensor element and the control device. Thus, as outlined above, the sensor element and the control device may be connected by one of a permanent connection and a releasable connection. More preferably, a permanent connection is used.

As outlined above, the sensor element preferably may be a flexible sensor element comprising a flexible substrate and at least two electrodes applied to the flexible substrate. The at least two electrodes preferably may comprise at least one working electrode, the working electrode having a conductive pad and at least one sensor material applied to the conductive pad. The sensor material may be adapted to perform at least one detection reaction in the presence of the analyte to be detected. The detection reaction may be adapted to change at least one measurable electrical property of the sensor material, such as an electrical property and/or an optical property. The at least two electrodes may further comprise at least one of a reference electrode and a counter electrode. The at least one reference electrode and the at least one counter electrode may be embodied as separate electrodes and/or may be embodied as a combined reference-counter-electrode.

The control device may have a rotational symmetry around a symmetry axis perpendicular to a surface of the sensor module which resides on a surface of the body of the user when the sensor module is in use. Thus, as an example, the control device may be encased by a housing, as outlined above, such as a plastic housing. The housing may have the rotational symmetry around a symmetry axis perpendicular to the surface of the sensor module. The rotational symmetry may provide specific advantages with regard to positioning of the housing and with regard to the option of equal access from all sides. Generally, however, any other type of geometric design is feasible.

The sensor module may comprise at least one self-adhesive pad adapted to bond the sensor module to the skin surface of the user. Thus, as an example, the self-adhesive pad may comprise a plaster and/or a self-adhesive tape. Before use of the sensor module, the self-adhesive pad may be covered by one or more liners which may be detached from the self-adhesive pad during application of the sensor module to the skin surface of the user. The control device, preferably the housing of the control device, may be located on top of the self-adhesive pad. Thus, the self-adhesive pad may be located in between the control device and the skin of the user. The sensor element may penetrate the self-adhesive pad.

Further preferred embodiments relate to the mechanical interfaces of the sensor module, the data reader module and the data transmission module as well as, optionally, to the mechanical interface of the alarm module. Thus, the sensor module mechanical interface and the data reader module mechanical interface or the data transmission module mechanical interface, as well as, optionally, the alarm module mechanical interface may be adapted to be connected by one of a form-fit connection and a force-fit connection. Thus, as outlined above, in a first alternative of possible configurations of the kit, the data reader module mechanical interface may be coupled to the sensor module mechanical interface. In a second alternative configuration, the data transmission module mechanical interface may be coupled to the sensor module mechanical interface. In a third alternative configuration, the alarm module mechanical interface may be coupled to the sensor module mechanical interface. These couplings, preferably, may be performed by one of a form-fit connection and a force-fit connection.

It shall be noted, however, that a data transfer between the sensor module and one or more or even all of the data reader module, the data transmission module or the optional alarm module not necessarily has to take place in a coupled state. Thus, as an example, one or more of the data reader module, the data transmission module or the alarm module may simply be held in close proximity to the sensor module in order to allow for a transfer of data and/or instructions, preferably by near-field communication.

The sensor module mechanical interface and the mechanical interface of the data reader module or the mechanical interface of the data transmission module preferably may be adapted to be connected by a dovetail guide. Thus, as outlined above, preferably, the housing of the sensor module may provide a rim, such as a circumferential protruding rim. The data reader module mechanical interface and/or the data transmission module mechanical interface may provide an appropriate guide for this rim, thereby generating a dovetail guide connection. Inversely, the housing of the sensor module may provide at least one groove, such as a circumferential groove. Correspondingly, the data reader module mechanical interface, the data transmission module mechanical interface or, optionally, the alarm module mechanical interface may provide at least one rail and/or protrusion which may engage the groove. Thus, as an example, the data reader module mechanical interface, the data transmission module mechanical interface or, optionally, the alarm module mechanical interface may provide at least one slot, wherein the housing of the sensor module may fully or partially be inserted into the slot, such as by a guide rail. Generally, the sensor module mechanical interface and one or more of the mechanical interfaces of the data reader module, the data transmission module and, optionally, the alarm module may be adapted to form a key-keyhole connection.

At least one of the mechanical interfaces of the data reader module and the data transmission module may contain an opening, preferably a slot, wherein the sensor module may fully or partially be inserted into the opening.

The mechanical interface of the data reader module and the mechanical interface of the data transmission module may each contain a slot inside a housing, such as a housing of the data reader module or a housing of the data transmission module, respectively, wherein the sensor module may at least partially be inserted into the slot. The slot may comprise a rail for guiding the sensor module into the slot. Preferably, the housing of the sensor module may be guided into the slot when the sensor module is applied to the skin surface of the user.

The mechanical interfaces of the data reader module and the data transmission module and, optionally, the alarm module, may be identical. Thus, as an example, the data reader module, the data transmission module and, optionally, the alarm module may comprise identical housings, with identical mechanical interfaces. In order to avoid confusion of the modules, the housings of the data reader module and the data transmission module and, optionally, the alarm module may have different colors, whereas the mechanical dimensions are identical. Thus, as an example, the data reader module may have a yellow housing, the data transmission module may have a gray housing, and the alarm module may have a red or orange housing, in order to avoid confusion and/or to facilitate a more intuitive use of the modules. Other embodiments are feasible.

The sensor module preferably may be a disposable sensor module. Thus, as an example, the sensor module may be embodied such that the sensor module may be disposed as an entity. As outlined above, preferably, the sensor module comprises a housing, which, preferably, may not be opened in a non-destructive fashion. Thus, preferably, the housing of the sensor module is a unitary piece containing all components of the control device, including the data collection device and the wireless near-field communication device as cheap, single-use components. The kit according to the present invention may comprise a plurality of exchangeable sensor modules.

Contrarily, the data reader module and the data transmission module and, optionally, the alarm module may be embodied as reusable units. Thus, preferably, the data reader module, the data transmission module and, optionally, the alarm module each may comprise a rechargeable and/or exchangeable energy storage device, such as a rechargeable and/or exchangeable battery and/or a rechargeable accumulator. In case an exchangeable battery is provided, preferably, the data reader module, the data transmission module and, optionally, the alarm module each comprise a housing which may be opened in a non-destructive way, in order to exchange the battery. In case a rechargeable energy storage device is provided, the data reader module, the data transmission module and, optionally, the alarm module may comprise a recharging device, which may be embodied as a wire-bound recharging device such as a plug and/or as a wireless charging device, such as an inductive recharging device.

In a further aspect of the present invention, a method for determining a concentration of at least one analyte in a body fluid of a user is disclosed. The method comprises a use of the kit according to the present invention, such as the kit according to one or more of the embodiments disclosed above or as disclosed in further detail below. The method further comprises at least one step of reversibly coupling the data reader module to the sensor module and transferring measurement data from the sensor module to the data reader module via wireless near-field communication. After the data transfer, the data reader module may be de-coupled from the sensor module. The method further comprises at least one step of reversibly coupling the data transmission module to the sensor module and transferring measurement data from the sensor module to the data transmission module via wireless near-field communication. The method may further comprise de-coupling the data transmission module from the sensor module. The coupling of the data reader module to the sensor module may take place before or after the coupling of the data transmission module to the sensor module. Thus, as an example, the user may, on one day, couple the data reader module to the sensor module, and, on another day, may couple the data transmission module to the sensor module. Generally, either the coupling of the data reader module or the coupling of the data transmission module or the coupling of the optional alarm module may take place. Further, the coupling of the data reader module to the sensor module and/or the coupling of the data transmission module to the sensor module each may take place only once or repeatedly. Once data are read out from the sensor module by one or more of the data reader module, the data transmission module or the optional alarm module, the data may fully or partially remain stored in the sensor module, too, or may fully or partially be erased from the sensor module after reading.

The method may further comprise at least one step of transferring measurement data from the data transmission module via wireless far-field communication to at least one external device.

The external device preferably may be selected from the group consisting of: a computer, such as a medical computer of a doctor or a medical staff; a computer network; a medical supervisor's computer; a medical network; a medication device, such as an insulin pump.

Optionally, in case the kit comprises an alarm module as outlined above, the method may further comprise at least one step of reversibly coupling the alarm module to the sensor module and transmitting data from the sensor module to the alarm module, wherein the data transmitted by the sensor module contains one or both of measurement data or alarm instructions. The method may further comprise at least one step of generating at least one alarm signal in response to the data transmitted by the sensor module. As further outlined above, in case the data transmitted by the sensor module contain measurement data, the method may comprise at least one step of evaluating the measurement data by the alarm module and determining whether at least one alarm condition is fulfilled as well as providing at least one alarm signal in case the at least one alarm condition is fulfilled. For further details, reference may be made to the disclosure of the alarm module as given above.

The kit and the method according to the present invention provide a large number of advantages over known devices for determining an analyte concentration, such as continuous monitoring glucose sensors. Thus, the sensor module itself can be kept at a very low level, maintaining a small volume and weight. Thus, in a most simple embodiment, the sensor module may comprise a plastic housing containing the electronic components of the control device. Further, a simple plaster may be used, for attaching the sensor module to the skin. Thus, primarily, the sensor module may be embodied as a disposable sensor element, such as a disposable patch. Still, the full functionality of modern analytical devices may be provided, even for professional use. Thus, by outsourcing functionality into the data reader module and the data transmission module and, optionally, the alarm module, data evaluation, data monitoring and alarm functions as well as user interactions may be provided. Thus, the sensor module itself may serve the sole purpose of data collection, such as over a period of use of the sensor element, whereas the data collection device and the data transmission device may allow for a retrospective data evaluation, such as by a medical expert. Still, an alarm function may be provided by coupling the optional alarm module to the sensor module, such as during times of low activities of the user, e.g. at night or during resting periods.

The wireless near-field communication device of the control device requires a minimum energy, only. Thus, generally, a reading of the measurement data may be performed even without a battery in case a passive device is provided and/or in case the battery is discharged. Thus, the energy supply of the sensor module may be kept at a minimum level. Still, by wireless near-field transmission of the measurement data to the data transmission module and from the data transmission module to an external device, or directly from the sensor module to the external device via wireless near-field communication, the full functionality of a data management device and/or an external computer may be used. The data transmission module, which may also be referred to as a communication module, may comprise a rechargeable and/or exchangeable energy storage device, such as a battery and/or an accumulator, and may be used repeatedly.

Further, the data transmission module may transfer the measurement data to remote devices, thereby allowing for data evaluation and/or a recognition of a critical medical status, such as a low glucose level and/or a high glucose level. Further, as an example, the data transmission module may be used during specific activities, such as during sports or exercising, in order to allow for training staff to supervise the user, such as by a remote computer communicating with the data transmission module when the data transmission module is coupled to the sensor module. Thus, as an example, an on-line monitoring of longdistance runners may be performed. Additionally or alternatively, an online monitoring of elderly people or inmates of hospitals or nursing facilities may be performed.

Still, the kit provides a high flexibility with regard to the optimum configuration of the system. Thus, the configuration of the kit may be adapted to the actual needs of the situation, by coupling the appropriate component of the kit to the sensor module. Thus, the sensor module may be used as a stand-alone device, for collection of measurement data, without any further device coupled to the sensor module. Alternatively, one of the data reading module, the data transmission module and the alarm module may be coupled to the sensor module, as the actual situation requires. Thus, for data collection, data storage or data evaluation purposes, the data reader module may be coupled to the sensor module. Alternatively, for data transmission to a remote computer or remote device, the data transmission module may be coupled to the sensor module. Alternatively, in situations in which a monitoring is required, such as in intensive care situations and/or during the night, the alarm module may be coupled to the sensor module. Thus, a high flexibility with regard to the actual configuration of the system exists. Further, as outlined above, a direct near-field communication with one or more devices such as the data management device may be performed, such as a smartphone. Thus, as an example, a reading on demand initiated by the data management device may be performed. Further, a near-field communication with a medication pump may be performed.

Summarizing the findings of the present invention, the following embodiments are preferred. Still, other embodiments are feasible.

Embodiment 1: A kit for determining a concentration of at least one analyte in a body fluid of a user, the kit comprising:
  a) a sensor module comprising
    i. at least one sensor element adapted to determine the concentration of the analyte, wherein the sensor element is at least partly implantable into a body tissue of the user;
    ii. at least one control device connected to the sensor element, wherein the control device comprises at least one data collection device adapted to collect measurement data acquired by using the sensor element, wherein the control device further comprises at least one wireless near-field communication device adapted to transmit measurement data, wherein the sensor module comprises a sensor module mechanical interface;
b) at least one data reader module adapted to receive measurement data transmitted by the sensor module via wireless near-field communication, wherein the data reader module comprises at least one data storage device and is adapted to store the measurement data;
c) at least one data transmission module adapted to receive measurement data transmitted by the sensor module via wireless near-field communication, wherein the data transmission module comprises at least one wireless far-field communication device, wherein the wireless far-field communication device is adapted to transmit at least part of the measurement data to an external device via wireless far-field communication;
wherein the data reader module and the data transmission module each comprise a mechanical interface adapted to reversibly engage the sensor module mechanical interface, thereby alternatively generating a fixed spatial relationship between the sensor module and the data reader module or the sensor module and the data transmission module.

Embodiment 2: The kit according to the preceding embodiment, wherein the kit further comprises:
d) at least one alarm module adapted to receive data transmitted by the sensor module via wireless near-field communication, wherein the data transmitted by the sensor module contain one or both of measurement data or alarm instructions, wherein the alarm module is adapted to generate at least one alarm signal in response to the data transmitted by the sensor module, wherein the alarm module comprises a mechanical interface adapted to reversibly engage the sensor module mechanical interface, as an alternative to the data reader module and the data transmission module, thereby generating a fixed spatial relationship between the sensor module and the alarm module.

Embodiment 3: The kit according to the preceding embodiment, wherein the data transmitted by the sensor module contain measurement data, wherein the alarm module is adapted to evaluate the measurement data and to determine whether at least one alarm condition is fulfilled and to provide the alarm signal in case the at least one alarm condition is fulfilled.

Embodiment 4: The kit according to the preceding embodiment, wherein the alarm module comprises at least one data processing element having a software code stored therein, with program means for subjecting the measurement data to the at least one alarm condition.

Embodiment 5: The kit according to any of the two preceding embodiments, wherein the alarm signal is selected from the group consisting of an acoustic alarm signal, an optical alarm signal and a vibrational alarm signal.

Embodiment 6: The kit according to any of the preceding embodiments, wherein the kit further comprises:
e) a portable data management device, wherein the portable data management device is adapted to directly or indirectly receive the measurement data and to at least partially display the measurement data.

Embodiment 7: The kit according to the preceding embodiment, wherein the portable data management device is further adapted to perform at least one data evaluation algorithm.

Embodiment 8: The kit according to any of the two preceding embodiments, wherein the data management device is adapted to automatically shut off a medication pump, specifically an insulin pump, in response to the measurement data.

Embodiment 9: The kit according to any of the three preceding embodiments, wherein the data management device is adapted to transmit data to the sensor module, preferably via near-field communication, preferably calibration data.

Embodiment 10: The kit according to any of the four preceding embodiments, wherein the portable data management device comprises at least one device selected from the group consisting of: a portable computer; a smartphone; a watch; a medication pump; a hand-held device for determining a concentration of the analyte in a body fluid, wherein the hand-held device is adapted to use at least one test element having at least one test field, wherein a sample of the body fluid is applicable to the test field.

Embodiment 11: The kit according to any of the five preceding embodiments, wherein the portable data management device comprises at least one user interface allowing for a user to insert commands.

Embodiment 12: The kit according to any of the six preceding embodiments, wherein the portable data management device comprises at least one data processing element adapted to apply the at least one data processing algorithm to the measurement data.

Embodiment 13: The kit according to any of the seven preceding embodiments, wherein the portable data management device comprises at least one database for storing the measurement data.

Embodiment 14: The kit according to any of the eight preceding embodiments, wherein the portable data management device is adapted to receive measurement data from the data transmission module via wireless far-field communication.

Embodiment 15: The kit according to any of the nine preceding embodiments, wherein the portable data management device is adapted to receive measurement data directly from the sensor module via wireless near-field communication.

Embodiment 16: The kit according to any of the ten preceding embodiments, wherein the data management device comprises at least one display element adapted to display a plurality of measurement data.

Embodiment 17: The kit according to any of the preceding embodiments, wherein the control device comprises an energy storage device.

Embodiment 18: The kit according to any of the preceding embodiments, wherein the control device comprises at least one data storage device.

Embodiment 19: The kit according to any of the preceding embodiments, wherein the wireless near-field communication device of the control device comprises at least one coil for inductive coupling.

Embodiment 20: The kit according to any of the preceding embodiments, wherein the wireless far-field communication device of the data transmission module comprises at least one radio transmitter.

Embodiment 21: The kit according to any of the preceding embodiments, wherein the data reader module comprises at least one interface adapted to at least partially transfer the measurement data to an external device.

Embodiment 22: The kit according to the preceding embodiment, wherein the interface comprises a wire-bound interface.

Embodiment 23: The kit according to the preceding embodiment, wherein the wire-bound interface comprises a plug.

Embodiment 24: The kit according to any of the three preceding embodiments, wherein the interface is selected from the group consisting of: a USB interface; an infrared interface; a Bluetooth interface.

Embodiment 25: The kit according to any of the preceding embodiments, wherein the control device comprises a closed housing.

Embodiment 26: The kit according to the preceding embodiment, wherein the closed housing is made of a plastic material.

Embodiment 27: The kit according to any of the two preceding embodiments, wherein the closed housing is made of a unitary piece of material.

Embodiment 28: The kit according to any of the three preceding embodiments, wherein the sensor module mechanical interface comprises at least one protrusion formed on an outer side of the housing.

Embodiment 29: The kit according to the preceding embodiment, wherein the protrusion comprises at least one protruding rim.

Embodiment 30: The kit according to the preceding embodiment, wherein the protruding rim is a circumferential protruding rim.

Embodiment 31: The kit according to any of the six preceding embodiments, wherein the housing comprises an opening through which an insertion tool for inserting the sensor element into the body tissue may penetrate the housing.

Embodiment 32: The kit according to the preceding embodiment, wherein the opening is a central opening.

Embodiment 33: The kit according to any of the two preceding embodiments, wherein the opening is selected from the group consisting of: a through-hole penetrating the housing along an axis of symmetry; an offset through-hole penetrating the housing offside an axis of symmetry; an oblique through-hole penetrating the housing along an axis of penetration, the axis of penetration forming an angle α with an axis of symmetry of the housing, wherein $0° < \alpha < 90°$, preferably $20° < \alpha < 70°$, more preferably $\alpha = 45°$.

Embodiment 34: The kit according to any of the preceding embodiments, wherein the kit further comprises
f) an insertion device, the insertion device comprising at least one skin-penetration element adapted to perforate a skin of the user and to guide the sensor element into the body tissue of the user.

Embodiment 35: The kit according to the preceding embodiment, wherein the skin-penetration element comprises at least one cannula.

Embodiment 36: The kit according to any of the two preceding embodiments, wherein the insertion device further comprises at least one driving mechanism for driving the skin-penetration element into the body tissue.

Embodiment 37: The kit according to any of the three preceding embodiments, wherein the insertion device comprises at least one mechanical interface adapted to engage the sensor module mechanical interface during insertion of the sensor element.

Embodiment 38: The kit according to any of the preceding embodiments, wherein the sensor element and the control device are connected by one of a permanent connection or a releasable connection.

Embodiment 39: The kit according to any of the preceding embodiments, wherein the sensor element is a flexible sensor element comprising a flexible substrate and at least two electrodes applied to the flexible substrate.

Embodiment 40: The kit according to the preceding embodiment, wherein the at least two electrodes comprise at least one working electrode, the working electrode having a conductive pad and at least one sensor material applied to the conductive pad, wherein the sensor material is adapted to perform at least one detection reaction in the presence of the analyte to be detected, wherein the detection reaction changes at least one measurable electrical property of the sensor material.

Embodiment 41: The kit according to any of the two preceding embodiments, wherein the at least two electrodes further comprise at least one of a reference electrode and a counter electrode.

Embodiment 42: The kit according to any of the preceding embodiments, wherein the control device has a rotational symmetry around a symmetry axis perpendicular to a surface of the sensor module which resides on a surface of the body of the user when the sensor module is in use.

Embodiment 43: The kit according to any of the preceding embodiments, wherein the sensor module comprises at least one self-adhesive patch adapted to bond the sensor module to a skin surface of the user.

Embodiment 44: The kit according to the preceding embodiment, wherein the control device is located on top of the self-adhesive patch.

Embodiment 45: The kit according to any of the two preceding embodiments, wherein the sensor element penetrates the self-adhesive patch.

Embodiment 46: The kit according to any of the preceding embodiments, wherein the sensor module mechanical interface and the mechanical interface of the data reader module or the mechanical interface of the data transmission module are adapted to be connected by at least one of a form-fit connection or a force-fit connection.

Embodiment 47: The kit according to any of the preceding embodiments, wherein the sensor module mechanical interface and the mechanical interface of the data reader module or the mechanical interface of the data transmission module are adapted to be connected by a dovetail guide.

Embodiment 48: The kit according to any of the preceding embodiments, wherein the sensor module mechanical interface and the mechanical interface of the data reader module or the mechanical interface of the data transmission module are adapted to form a key—keyhole connection.

Embodiment 49: The kit according to any of the preceding embodiments, wherein the at least one of the mechanical interface of the data reader module and the mechanical interface of the data transmission module contain an opening, wherein the sensor module may fully or partially be inserted into the opening.

Embodiment 50: The kit according to any of the preceding embodiments, wherein the mechanical interface of the data reader module and the mechanical interface of the data transmission module each contain a slot inside a housing of the data reader module and the data transmission module, respectively, wherein the sensor module may at least partially be inserted into the slot.

Embodiment 51: The kit according to the preceding embodiment, wherein the slot comprises a rail for guiding the sensor module into the slot.

Embodiment 52: The kit according to any of the preceding embodiments, wherein the mechanical interface of the data reader module and the mechanical interface of the data transmission module are identical.

Embodiment 53: The kit according to any of the preceding embodiments, wherein the sensor module is a disposable sensor module.

Embodiment 54: The kit according to the preceding embodiment, wherein the kit comprises a plurality of exchangeable sensor modules.

Embodiment 55: The kit according to any of the preceding embodiments, wherein the data reader module and the data transmission module are reusable units.

Embodiment 56: A method for determining a concentration of at least one analyte in a body fluid of a user, the method comprising a use of the kit according to one of the preceding embodiments, the method further comprising at least one step of reversibly coupling the data reader module to the sensor module and transferring measurement data from the sensor module to the data reader module via wireless near-field communication, the method further comprising at least one step of reversibly coupling the data transmission module to the sensor module and transferring measurement data from the sensor module to the data transmission module via wireless near-field communication.

Embodiment 57: The method according to the preceding embodiment, the method further comprising at least one step of transferring measurement data from the data transmission module via wireless far-field communication to at least one external device.

Embodiment 58: The method according to the preceding embodiment, wherein the external device is selected from the group consisting of: a computer; a computer network; a medical supervisor's computer; a medical network; a medication device; a remote control for a medication pump, specifically an insulin pump and/or a micro pump; a smartphone.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

In the Figures:

FIG. 1 shows an overview of a potential embodiment of a kit according to the present invention;

FIG. 2 shows an interaction between a sensor module and a data reader module of the kit according to the present invention;

FIGS. 6A to 6D show different use of components of the kit according to the present invention, further comprising an insertion device for inserting a sensor element into a body tissue of the user.

DETAILED DESCRIPTION OF THE EMBODIMENTS

Figure 3:
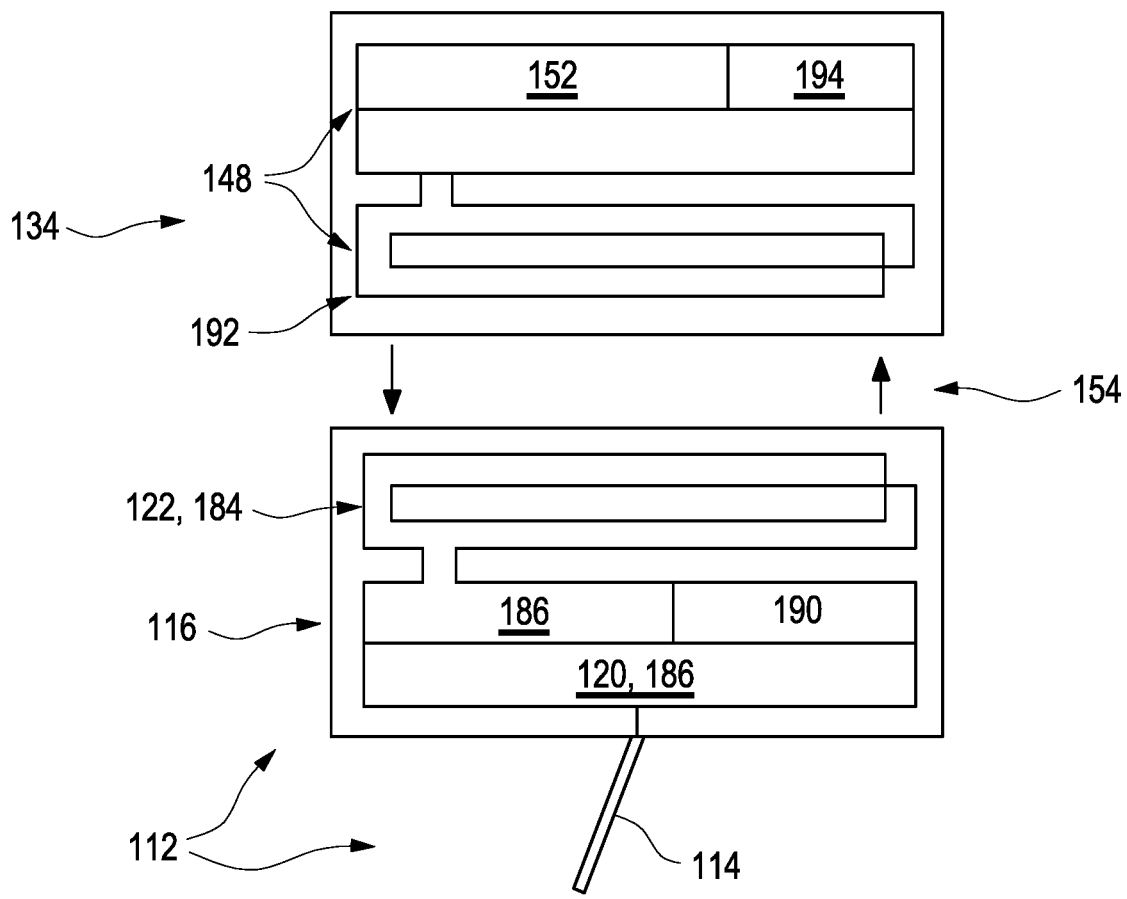
FIGS. 3A to 3D show potential embodiments of interactions of a sensor module, a data transmission module and an external device of an embodiment of the kit according to the present invention.
Figure 3:
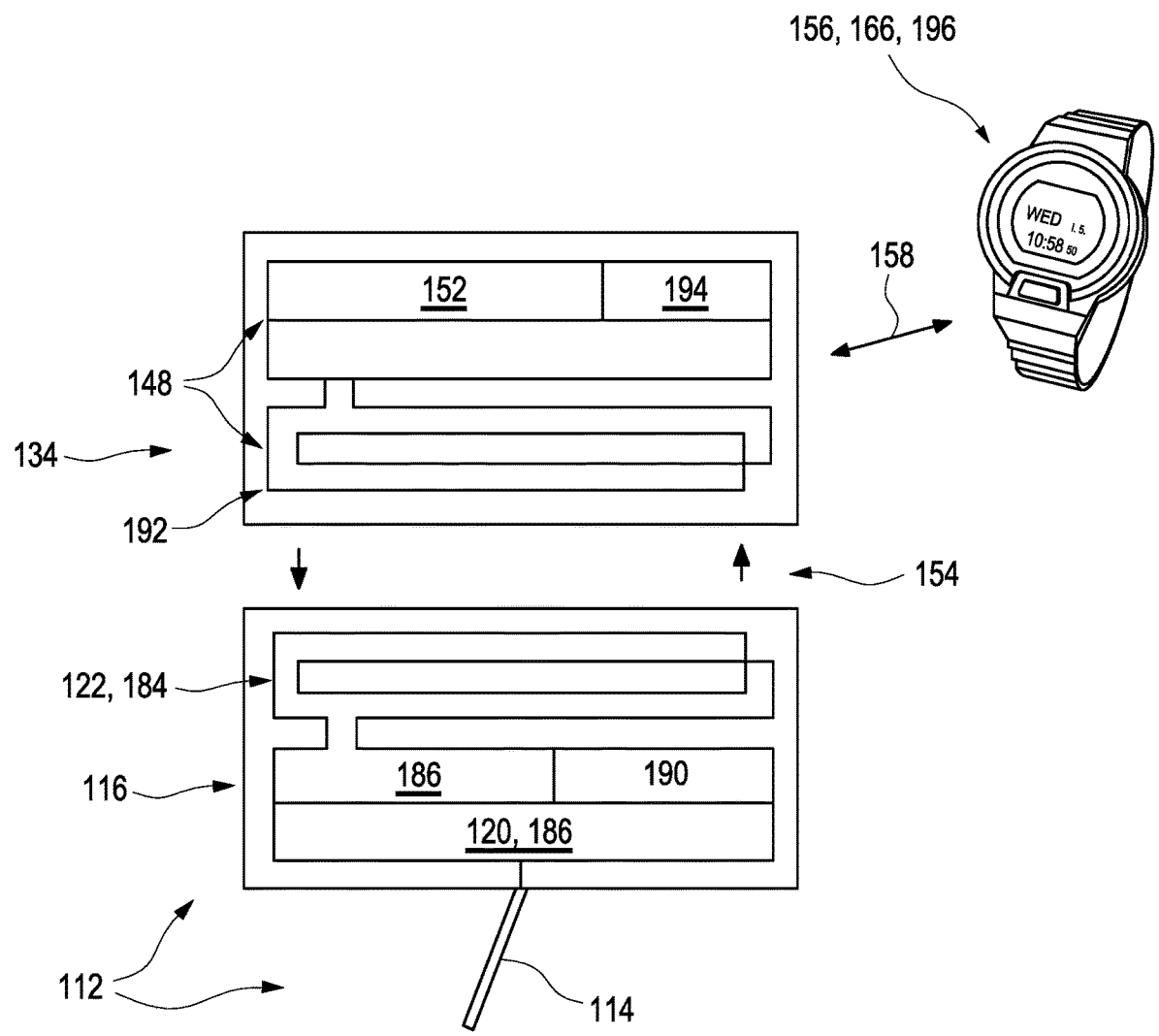
Figure 3:
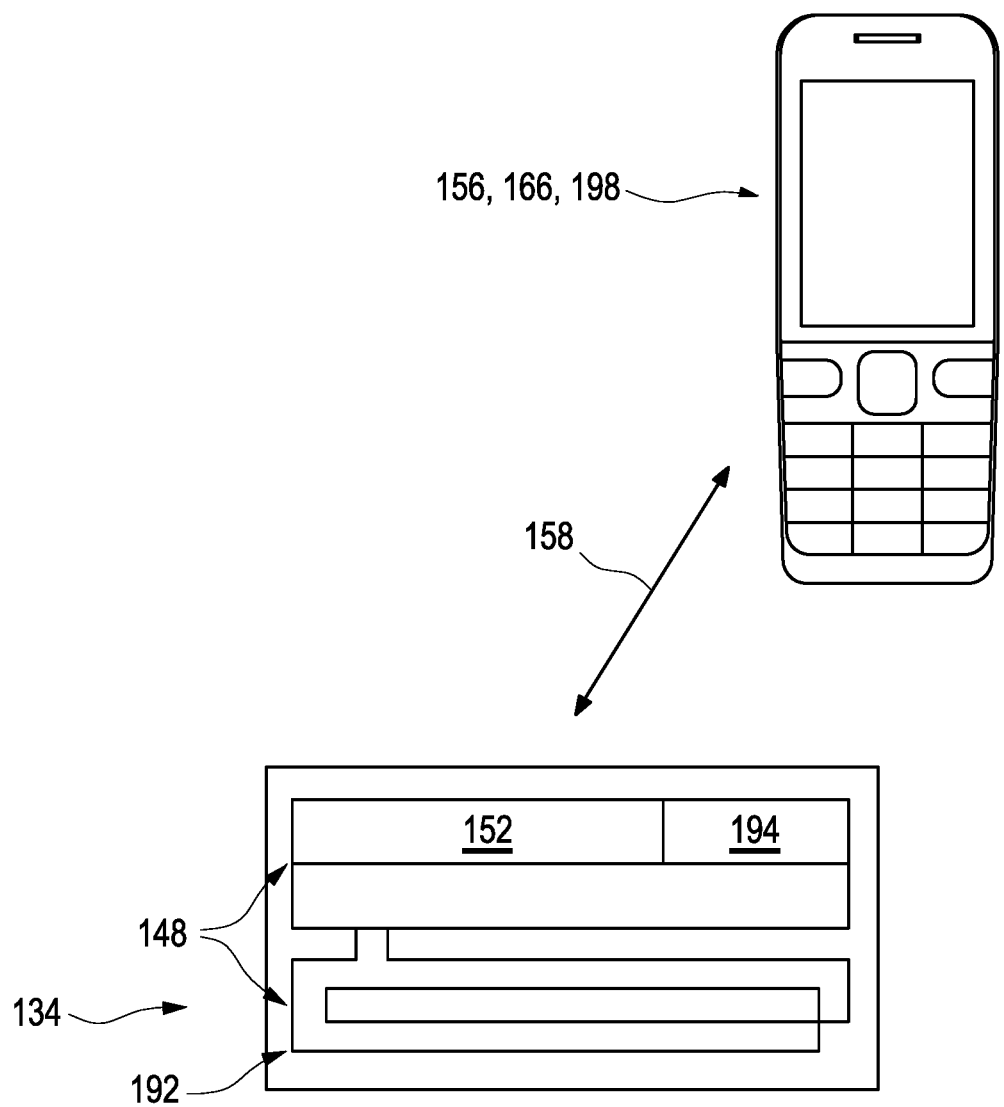

In FIG. 1, various components of a kit 110 for determining a concentration of at least one analyte in a body fluid of a user are shown. The kit comprises a sensor module 112 which, in the middle of FIG. 1, is depicted in a stand-alone fashion. The sensor module comprises a sensor element 114 adapted to be at least partially implanted into a body tissue of the user. The sensor element 114 is connected to a control device 116 encapsulated by a housing 118. The control device 116, as will be outlined in further detail below, comprises at least one data collection device 120 and at least one wireless near-field communication device 122. The sensor module 112 further comprises at least one self-adhesive patch 124 adapted to mount the sensor module 112 to a skin surface of a user.

The sensor module 112 further comprises a sensor module mechanical interface 126. In this specific embodiment, as an example the sensor module mechanical interface 126 comprises a circumferential protruding rim 128, which may be part of the housing 118, as depicted in FIG. 1, or, which may be attached to the housing 118.

The sensor module 112, as depicted in FIG. 1, may have a rotational symmetry and, preferably, may have a volume of less than 2 cm$^3$. Further, the housing 118 may have a central opening 130, through which an insertion tool for inserting the sensor element 114 into the body tissue may penetrate the housing 118.

The kit 110 further comprises a data reader module 132, a data transmission module 134 and, optionally, an alarm module 136. These modules 132, 134, 136 may generally have identical or similar geometric shapes and dimensions. Still, the modules 132, 134, 136 may be distinct in terms of color and/or labeling or marking.

Each of the modules 132, 134, 136 has a mechanical interface for reversibly coupling the respective module to the sensor module 112, thereby providing a fixed spatial relationship between the sensor module 112 and the respective module 132, 134, 136. In this specific example, a form-fit connection may be provided. Thus, the data reader module 132 has a data reader module mechanical interface 138, the data transmission module 134 has a data transmission module mechanical interface 140, and the alarm module 136 has an alarm module mechanical interface 142. Each of the mechanical interfaces 138, 140, 142, in this specific embodiment, comprises a slot 144 having a guide rail 146 which may engage the circumferential protruding rim 128 of the sensor module 112. In the exemplary embodiment shown in FIG. 1, the data reader module 132 is shown in a de-coupled state, whereas the data transmission module 134 and the alarm module 136 are shown in a state in which a sensor module 112 is inserted into the slot 144, thereby providing a fixed spatial relationship between the sensor module 112 and the respective module 134, 136.

As will be outlined in further detail below, the data reader module 132 is adapted to receive measurement data transmitted by the sensor module 112 via wireless near-field communication. For this purpose, the data reader module 132 may comprise a wireless near-field communication device 148. Similarly, the data transmission module 134 and, optionally, the alarm module 136 each may comprise a wireless near-field communication device 148.

The data reader module 132 further comprises at least one data storage device 150 and is adapted to store measurement data transmitted by the sensor module 112 via wireless near-field communication. The at least one data transmission module 134 comprises at least one wireless far-field communication device 152, such as at least one radio module, wherein the wireless far-field communication device 152 is adapted to transmit at least part of the measurement data to an external device via wireless far-field communication. As an example, in FIG. 1, a wireless near-field communication between the sensor module 112 and the data transmission module 134 is denoted by reference number 154, as an exemplary embodiment, an external device is denoted by reference number 156. The wireless far-field communication between the data transmission module 134 and the external device 156, as an exemplary embodiment, is denoted by reference number 158.

The alarm module 136 may comprise at least one data processing element 160 and may be adapted to evaluate the measurement data, in order to determine whether at least one alarm condition is fulfilled. Further, the alarm module 136 is adapted to provide at least one alarm signal in case the at least one alarm condition is fulfilled. For this purpose, the alarm module 136 may comprise at least one alarm signal generator 162, such as an alarm signal generator 162 selected from the group consisting of an acoustic alarm signal generator, an optical alarm signal generator and a vibrational alarm signal generator. Thus, as an example, in case an alarm condition is determined to be fulfilled, the alarm module 136 may vibrate and/or give an acoustic alarm signal, such as an alarm sound, and/or may provide an optical alarm signal, such as by providing repeated flashings of light and/or by changing an illumination state.

The modules 132, 134 and 136 may be designed as reusable components and, preferably, each may have a housing 164. As an example, the housings 164 may provide the option of being opened, in order to exchange a battery.

As depicted in the exemplary embodiment of FIG. 1, the kit 110 may further comprise at least one portable data management device 166. As outlined above, the portable data management device 166 preferably may be a hand-held device, such as a hand-held computer and/or a hand-held communication device, preferably a smartphone. The portable data management device 166 may be identical to the external device 156 or may form a separate component, independent from the external device 156. As will be outlined in further detail below, the portable data management device 166 may, in one option, directly communicate with the sensor module 112 via wireless near-field communication 154, in order to receive measurement data. Additionally or alternatively, however, the portable data management device 166 may communicate with the data transmission module 134 via wireless far-field communication 158, as indicated for the external device 156 in FIG. 1.

The portable data management device 166 may comprise at least one user interface 168, allowing for a user to insert commands and/or information. As indicated in FIG. 1, the user interface 168 may comprise a touchscreen. The portable data management device 166 may further comprise at least one display element 170, for displaying data and/or measurement results and/or additional information.

The portable data management device 166, as outlined above, may comprise at least one data processing element 172, such as at least one processor, adapted to apply at least one data processing algorithm to the measurement data. The portable data management device 166 may further comprise at least one data storage device and/or memory, such as at least one database, for storing the measurement data.

The portable data management device 166 is adapted to apply at least one data processing algorithm to the measurement data. As outlined above, this data processing algorithm may imply a visualization of measurement data, such as a graphical display of measurement curves. Further, one or more items of additional information may be generated by evaluating the measurement data, such as by comparing the measurement data with one or more threshold values, in order to generate information on medical states of the user.

For communicating via wireless near-field communication, the portable data management device 166 may optionally comprise at least one wireless near-field communication device 148. For wireless far-field communication, the portable data management device 166 may further comprise at least one wireless far-field communication device 152, as indicated in FIG. 1.

In the following, the specific interactions of the components of the kit 110 are disclosed in exemplary details. Thus, in FIG. 2, an embodiment of interaction of the data reader module 132 with the sensor module 112 is depicted schematically, allowing for a retrospective reading of measurement data and/or a retrospective evaluation of measurement data. As indicated above, the sensor module 112 as depicted in FIG. 2 may be operated such that the sensor element 114 is at least partially implanted into a body tissue 174 of the user. In this state or even in a state in which the sensor element 114 is not implanted into the body tissue 174, the sensor module 112 may communicate with the data reader module 132 via wireless near-field communication 154, in order to transmit measurement data. The data reader module 132 may store the measurement data in the data storage device 150. At a later point in time, the data reader module 132 may fully or partially transfer the measurement data via at least one interface 176 to an external device 156 having a corresponding interface 178. The external device 156, as an example, may comprise a computer such as a personal computer, a smartphone, a controller or a blood glucose meter. Other options are listed above. The interfaces 176, 178 may allow for a data transfer 180, which may be a wire-bound data transfer and/or a wireless data transfer. As an example, the interface 176 may comprise a plug which may be plugged into a corresponding plug of the external device 156, such as a USB plug. Additionally or alternatively, a wireless transfer may take place, such as a data transfer 180 via infrared data transmission, Bluetooth or other types of wireless data transmission. Specifically, the data reader module 132 may be used in the same fashion as a USB data stick. The user, specifically the patient, may collect measurement data on a regular basis, by using the data reader module 132, and may transfer the measurement data to a medical supervisor, such as a doctor, by simply carrying the data reader module 132 to the medical supervisor's office. Additionally or alternatively, the data reader module 132 may provide sufficient storage capability for storing measurement data over an elongated time period, such as over one week or several weeks.

In FIGS. 3A to 3D, various interactions of the sensor module 112 with the data transmission module 134 and, optionally, one or more external devices 156 and/or portable data management devices 166 are depicted. Thus, generally, FIG. 3A shows a schematic interaction of these components, in a fashion similar to the setup shown in FIG. 2. Thus, generally, with regard to the sensor module 112 and with regard to the data transmission module mechanical interface 148, reference may be made to the description of FIGS. 1 and 2 above. Measurement data may be transferred from the sensor module 112 to the data transmission module 134 via wireless near-field communication 154, such as in a state in which the data transmission module 134 is mechanically coupled to the sensor module 112. Thus, generally, in this embodiment or other embodiments of the present invention, the mechanical interfaces 138, 140 and 142 of the modules 132, 134 and 136 may be adapted such that, when the respective modules 132, 134 and 136 are coupled to the sensor module mechanical interface 126, a wireless near-field communication 154 between the sensor module 112 and the respective module 132, 134 and 136, respectively, is possible. Thus, the mechanical interfaces 126 and 138, 140 and 142, respectively, may be adapted such that in a coupled state, the distance between the wireless near-field communication device 122 of the sensor module 112 and the wireless near-field communication devices 148 of the respective modules 132, 134 and 136 is closer than 1 cm.

As outlined in FIG. 3A, the data transmission module 134, by using its wireless far-field communication device 152, may transmit at least part of the measurement data via wireless far-field communication 158 to one or more external devices 156. Thus, an on-line monitoring may be possible, as opposed to the retrospective data evaluation provided by the data reader module 132. As outlined above, the external device 156 may have a corresponding wireless far-field communication device 182. As an example, the wireless far-field communication devices 152, 182 may be designed as radio transmitters, radio receivers and/or radio transceivers.

The external device 156, as outlined above, may be a stationary external device or a portable external device. Thus, in the latter case, the portable device may be the portable data management device 166, as outlined above. Specifically, the external device 156 may comprise one or more of a smartphone, a tablet PC, an app on a smartphone or a tablet PC, a controller and/or data manager, a personal computer, a medication pump (specifically an insulin pump) and/or a spot meter using one or more test elements for determining the analyte concentration, such as a blood glucose meter. Other options are possible. Specifically, in this embodiment or other embodiments, the external device 156 may provide at least one data evaluation function and/or at least one alarm function.

In FIG. 3B, several details of a potential setup of the near-field communication between the data transmission module 134 and the sensor module 112 are depicted. The wireless near-field communication 154 may be unidirectional or bidirectional. Thus, in a unidirectional fashion, only a transmission of the measurement data from the sensor module 112 to the data transmission module 134 may take place. In a bidirectional mode, however, the data transmission module 134 may transmit commands and/or information to the sensor module 112. Additionally, the data transmission module 134 may transmit energy to the sensor module 112, such as via inductive coupling.

As depicted in FIG. 3B, the wireless near-field communication device 122 of the sensor module 112 may comprise an antenna 184. The data collection device 120 may comprise one or more signal processing devices 186. Further, one or more potentiostats and/or other electronic measurement components may be present.

Further, the control device 116 of the sensor module 112 may comprise one or more data storage devices 188, such as one or more volatile and/or non-volatile data memory components.

The sensor module 112 may further comprise one or more energy storage devices 190. Thus, as an example, one or more batteries and/or accumulators may be implemented into the sensor module 112.

The wireless near-field communication device 148 of the data transmission module 134 may comprise one or more antennae 192. Further, the data transmission module 134 may comprise one or more energy storage devices 194, such as one or more accumulators and/or one or more batteries. Preferably, the at least one energy storage device 194 is rechargeable and/or replaceable.

The data transmission module 134 may further comprise at least one data storage device, which is not depicted in FIG. 3B. Further, as outlined above, the data transmission module 134 comprises the wireless far-field communication device 152. Therein, several standards for wireless far-field communication may be used. As an example, radio standards may be used, such as the Bluetooth standard, specifically the Bluetooth Low Energy standard (BTLE) and/or radio standards, such as GSM. These options are depicted in FIGS. 3C and 3D. Thus, as an exemplary embodiment, in FIG. 3C, a wireless far-field communication 158 with an external device 156 is depicted, wherein, in this embodiment, the external device 156 may be embodied as a portable data management device 166, specifically as a watch 196, more preferably a wrist watch. Therein, preferably, a Bluetooth communication is chosen, such as BTLE.

In FIG. 3D, an embodiment is shown without the sensor module 112, which may be present additionally, wherein the wireless far-field communication 158 between the data transmission module 134 and an external device 156, such as a smartphone 198, may take place via known radio standards for telecommunication purposes, such as one or more of GSM, UMTS and LTE.

Figure 4:
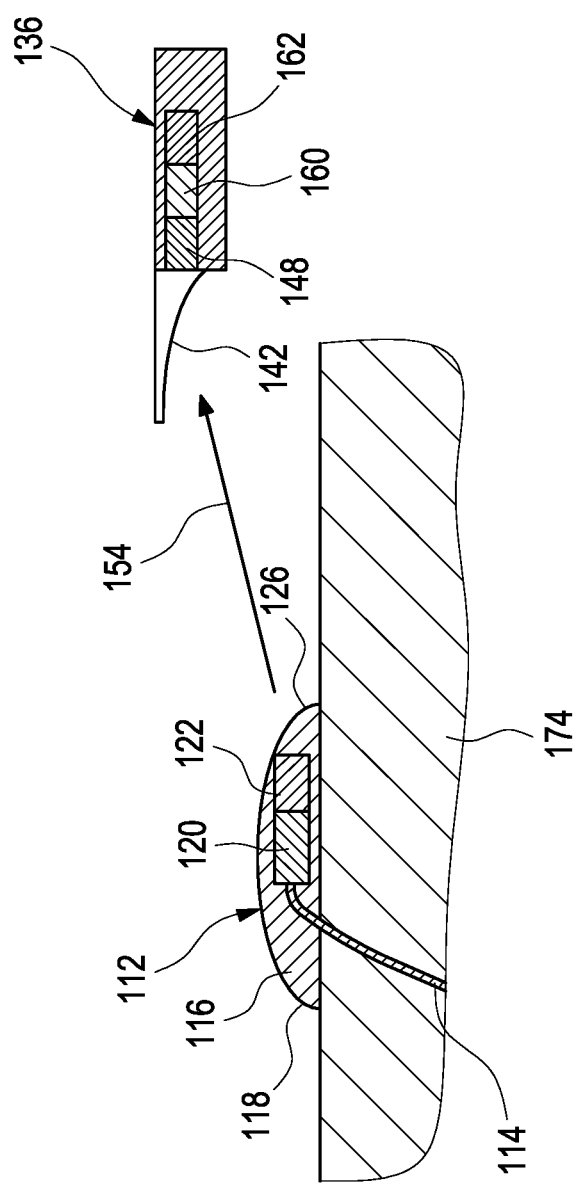
FIG. 4 shows an interaction of the sensor module and an alarm module.

In FIG. 4, in a similar setup as shown in FIGS. 2 and 3A, an interaction of the sensor module 112 with the alarm module 136 is depicted. Therein, in a state in which the alarm module mechanical interface 142 is coupled to the sensor module mechanical interface 126, the sensor module 112 may transmit measurement data to the alarm module 136 via wireless near-field communication 154. The alarm module 136, as outlined above, comprises the data processing element 160 which is adapted to evaluate the measurement data and to determine whether at least one alarm condition is fulfilled. Further, the alarm module 136 comprises the alarm signal generator 162, in order to provide at least one alarm signal in case the at least one alarm condition is fulfilled. Thus, optical, vibrational or acoustic signals or any arbitrary combination thereof may be provided.

Figure 5:
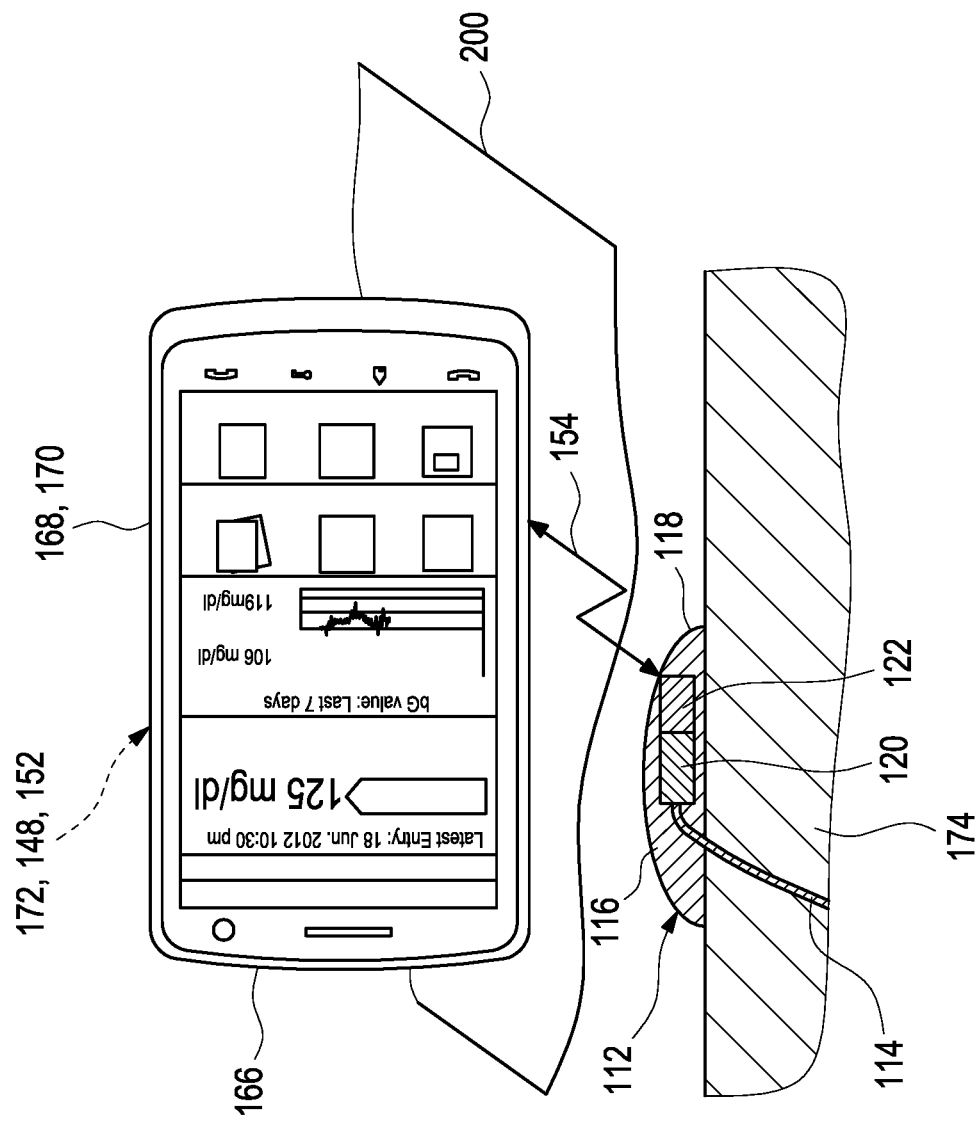
FIG. 5 shows an interaction of the sensor module and a portable data management device.

In FIG. 5, a further option of communication between the sensor module 112 and the optional portable data management device 166 is depicted. In this embodiment, as outlined above, the portable data management device 166 itself may comprise at least one wireless near-field communication device 148, as is the case in modern smartphones. In this option, the sensor module 112 may transmit data to the portable data management device 166 via near-field communication 154, which may take place over short distances, even through clothing 200.

As outlined above, the kit 100 may further comprise at least one insertion device. In FIGS. 6A to 6D, several views of components of the kit 110 are depicted, denoting potential details of the insertion. Thus, 6C again shows a potential embodiment of the sensor module 112, which may comprise the opening 130, preferably the central opening 130, preferably a through-hole. For details of the sensor module 112, reference may be made to FIG. 1 above.

In a state of delivery, the kit may comprise an insertion device 202, which may comprise at least one skin penetration element 204, such as at least one cannula 206. In FIGS. 6A and 6D, various embodiments of the sensor module 112, with the cannula 206 penetrating the opening 130 of the housing 118 of the sensor module 112, are depicted.

As depicted in FIG. 6B, the insertion device 202 may further comprise at least one driving mechanism 208 for driving the skin-penetration element 204 into the body tissue 174. As an example, the driving mechanism may comprise at least one actuator 210 having an actuator mechanical interface 212 adapted to engage the sensor module 112 and/or the skin-penetration element 204. The actuator 210 may be a spring-loaded actuator adapted to move within a guide rail 214 of a frame 216 of the insertion device 202. The insertion device 202 may further comprise a trigger 218 which may be pressed onto a skin surface of the user, in order to trigger a driving action of the actuator 210 and to drive the skin-penetration element 204 into the body tissue 174, thereby implanting the sensor element 114 into the body tissue 174. After insertion of the sensor element 114, the actuator 210 may be pulled back out of the body tissue 174, wherein the sensor element 114 remains within the body tissue 174. During this reverse action, the skin-penetration element 204 may be retracted from the opening 130, wherein the module 112, with the self-adhesive patch 124 sticking to the skin of the user, remains on the skin surface of the user.

The kit 110 according to the embodiment shown in the figures, with the sensor module 112, the data reader module 132, the data transmission module 134, the optional module 136 and the optional portable data management device 166 as well as the optional insertion device 202, allows for a number of preferred operations. Thus, during everyday use or during sports activities, the sensor module 112 may be worn as a stand-alone application, with maximum comfort for the user. The modules 132, 134 and 136, respectively, may be coupled to the sensor module 112 in regular or irregular time intervals, adapted to the personal needs.

Thus, during the night, the sensor module 112 may be coupled to one of the data reader module 132, the data transmission module 134 or the alarm module 136. Thus, as an example, when coupled to the data transmission module 134, the data transmission module 134 may communicate measurement data to a data manager, a smartphone with a monitoring application (such as a CGM app), a personal computer or other external devices 156. The external device may be adapted to give alarms in case an alarm condition is fulfilled, such as a hypoglycemic level and/or a hyperglycemic level.

Similarly, the alarm module 136 may be worn during the night and/or during sports activities, as an intelligent patch with all electronics and algorithms on board, in order to give striking alarms when one or more alarm conditions are fulfilled, such as in case hypoglycemic and/or hyperglycemic levels are detected. Thus, the alarm module may wake up the user during the night, in case an alarm condition is fulfilled, such as by giving a vibrational alarm and/or an alarm sound.

The coupling of the data reader module 132 to the sensor module 112 allows for a retrospective reading and/or evaluation of data. The data reading may be performed on a sporadic basis, since, preferably, the sensor module 112 itself may be able to store measurement data over extended time periods, such as over several hours, several days or even several weeks, such as for seven days or longer. On a regular or irregular basis, such as during day time, the data reader module 112 may communicate with the sensor module 112 and may read out data in short time. The data reader module 132 may be coupled, subsequently or simultaneously, to an external device 156, such as a smartphone with a specific application, such as a CGM application, or may be read out via a computer, such as a personal computer in a doctor's office. The data reader module 134 may be kept a low level, without any display and/or user interface. However, as outlined above, the data reader module 132 preferably provides one or more electronic interfaces, such as one or more wireless and/or wire-bound interfaces, for data transfer 180 to an external device 156, such as one or more USB connectors.

The additional option of using an intelligent sensor module 112 in direct conjunction with a portable data management device 166 allows for a direct reading of measurement data via wireless near-field communication. Thus, a smartphone may be used, having a wireless near-field communication device 148, for data transfer of measurement data via wireless near-field communication 154 through clothing 200. The portable data management device 166, such as a smartphone, may comprise one or more applications, such as one or more monitoring apps, for evaluating the data.

The additional option of providing an insertion device 202 within the kit 110 may complete the flexibility of the kit 110. Thus, as an insertion device 202, commercially available insertion devices which typically are used for insertion of transfusion kits and/or cannulas for medication pumps such as insulin pumps may be used for inserting the sensor element 114. Thus, the insertion effort may be kept at a very low level, and known insertion devices may be used, such as insertion devices many patients are familiar with, such as insertion devices for a cannula for insulin pumps. Thus, specifically, an additional training may be avoided. Specifically, the sensor module 112 may be designed as a disposable sensor module, and the kit 110 may comprise a plurality of exchangeable and disposable sensor modules 112.

LIST OF REFERENCE NUMBERS 110 kit for determining a concentration of an analyte in a body fluid of a user
112 sensor module
114 sensor element
116 control device
118 housing
120 data collection device
122 wireless near-field communication device
124 self-adhesive patch
126 sensor module mechanical interface
128 circumferential protruding rim
130 opening
132 data reader module
134 data transmission module
136 alarm module
138 data reader module mechanical interface
140 data transmission module mechanical interface
142 alarm module mechanical interface
144 slot
146 guide rail
148 wireless near-field communication device
150 data storage device
152 wireless far-field communication device
154 wireless near-field communication
156 external device
158 wireless far-field communication
160 data processing element
162 alarm signal generator
164 housing
166 portable data management device
168 user interface
170 display
172 data processing element 174 body tissue
176 interface
178 interface
180 data transfer
182 wireless far-field communication device
184 antenna
186 signal processing device
188 data storage device
190 energy storage device
192 antenna
194 energy storage device
196 watch
198 smartphone
200 clothing
202 insertion device
204 skin-penetration element
206 cannula
208 driving mechanism
210 actuator
212 actuator mechanical interface
214 guide rail
216 frame
218 trigger

The invention claimed is:

1. A kit for determining a concentration of at least one analyte in a body fluid of a user, the kit comprising:
   a) a sensor module comprising
      i. at least one sensor element adapted to determine the concentration of the analyte, wherein the sensor element is at least partly implantable into a body tissue of the user;
      ii. at least one control device connected to the sensor element, wherein the control device comprises at least one data collection device adapted to collect measurement data acquired by using the sensor element, wherein the control device further comprises at least one wireless near-field communication device adapted to transmit measurement data,
wherein the sensor module comprises a sensor module mechanical interface;
   b) at least one data reader module adapted to receive measurement data transmitted by the sensor module via wireless near-field communication, wherein the data reader module comprises at least one data storage device and is adapted to store the measurement data;
   c) at least one data transmission module adapted to receive measurement data transmitted by the sensor module via wireless near-field communication, wherein the data transmission module comprises at least one wireless far-field communication device,
wherein the wireless far-field communication device is adapted to transmit at least part of the measurement data to an external device via wireless far-field communication;
wherein the data reader module and the data transmission module are separate components and each comprises a mechanical interface adapted to reversibly engage the sensor module mechanical interface, thereby alternatively generating a fixed spatial relationship between the sensor module and the data reader module or the sensor module and the data transmission module.

2. The kit according to claim 1, wherein the kit further comprises:
   d) at least one alarm module adapted to receive data transmitted by the sensor module via wireless near-field communication, wherein the data transmitted by the sensor module contain one or both of measurement data or alarm instructions, wherein the alarm module is adapted to generate at least one alarm signal in response to the data transmitted by the sensor module, wherein the alarm module comprises a mechanical interface adapted to reversibly engage the sensor module mechanical interface, as an alternative to the data reader module and the data transmission module, thereby generating a fixed spatial relationship between the sensor module and the alarm module.

3. The kit according to claim 2, wherein the data transmitted by the sensor module contain measurement data, wherein the alarm module is adapted to evaluate the measurement data and to determine whether at least one alarm condition is fulfilled and to provide the alarm signal in case the at least one alarm condition is fulfilled.

4. The kit according to claim 1, wherein the kit further comprises:
   e) a portable data management device, wherein the portable data management device is adapted to directly or indirectly receive the measurement data and to at least partially display data.

5. The kit according to claim 4, wherein the portable data management device is adapted to receive the measurement data from the data transmission module via wireless far-field communication.

6. The kit according to claim 4, wherein the portable data management device is adapted to receive measurement data directly from the sensor module via wireless near-field communication.

7. The kit according to claim 1, wherein the wireless far-field communication device of the data transmission module comprises at least one radio transmitter.

8. The kit according to claim 1, wherein the data reader module comprises at least one interface adapted to at least partially transfer the measurement data to an external device.

9. The kit according to claim 1, wherein the control device comprises a closed housing, wherein the sensor module mechanical interface comprises at least one protrusion formed on an outer side of the housing.

10. The kit according to claim 1, wherein the kit further comprises
    f) an insertion device, the insertion device comprising at least one skin-penetration element adapted to perforate a skin of the user and to guide the sensor element into the body tissue of the user.

11. The kit according to claim 1, wherein the sensor module mechanical interface and the mechanical interface of the data reader module or the mechanical interface of the data transmission module are adapted to be connected by one of a form-fit connection and a force-fit connection.

12. The kit according to claim 1, wherein the sensor module mechanical interface and the mechanical interface of the data reader module or the mechanical interface of the data transmission module are adapted to be connected by a dovetail guide.

13. The kit according to claim 1, wherein the mechanical interface of the data reader module and the mechanical interface of the data transmission module each contain a slot inside a housing of the data reader module and the data transmission module, respectively, wherein the sensor module may at least partially be inserted into the slot.

14. The kit according to claim 1, wherein the sensor module is a disposable sensor module.

15. The kit according to claim 1, wherein the data reader module and the data transmission module are reusable units.

16. A method for determining a concentration of at least one analyte in a body fluid of a user, the method comprising a use of the kit according to claim 1, the method further comprising at least one step of reversibly coupling the data reader module to the sensor module and in transferring measurement data from the sensor module to the data reader module via wireless near-field communication, the method further comprising at least one step of reversibly coupling the data transmission module to the sensor module and transferring measurement data from the sensor module to the data transmission module via wireless near-field communication.

17. The method according to claim 16, the method further comprising at least one step of transferring measurement data from the data transmission module via wireless far-field communication to at least one external device.

* * * * *